US008055514B2

(12) United States Patent  (10) Patent No.: US 8,055,514 B2
Elsholz  (45) Date of Patent: Nov. 8, 2011

(54) USER-CENTRIC METHODOLOGY FOR NAVIGATING THROUGH AND ACCESSING DATABASES OF MEDICAL INFORMATION MANAGEMENT SYSTEM

(75) Inventor: John F. Elsholz, Sandy, UT (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 965 days.

(21) Appl. No.: 11/274,002

(22) Filed: Nov. 15, 2005

(65) Prior Publication Data

US 2007/0022086 A1   Jan. 25, 2007

Related U.S. Application Data

(60) Provisional application No. 60/700,434, filed on Jul. 19, 2005.

(51) Int. Cl.
*G06Q 10/00* (2006.01)
*G06Q 50/00* (2006.01)
*G06Q 40/00* (2006.01)
(52) U.S. Cl. ........................................ 705/3; 705/2; 705/4
(58) Field of Classification Search .................. 705/2–4
See application file for complete search history.

(56) References Cited

U.S. PATENT DOCUMENTS

| 4,500,777 | A | * | 2/1985 | Drexler ........................ 235/487 |
| 4,962,491 | A | * | 10/1990 | Schaeffer ....................... 368/21 |
| 5,337,290 | A | * | 8/1994 | Ventimiglia et al. ............ 368/10 |
| 5,499,293 | A | * | 3/1996 | Behram et al. .................. 705/76 |
| 5,579,393 | A | * | 11/1996 | Conner et al. ................. 713/176 |
| 5,708,851 | A | * | 1/1998 | Togawa .......................... 710/52 |
| 5,715,449 | A | | 2/1998 | Peters, Jr. et al. ............. 395/613 |
| 6,157,914 | A | * | 12/2000 | Seto et al. ......................... 705/3 |
| 6,192,112 | B1 | * | 2/2001 | Rapaport et al. ........... 379/88.22 |
| 6,381,579 | B1 | | 4/2002 | Gervais et al. ................... 705/8 |
| 6,411,999 | B1 | | 6/2002 | Tinkler ......................... 709/224 |
| 6,681,003 | B2 | * | 1/2004 | Linder et al. ............. 379/106.02 |
| 6,801,916 | B2 | | 10/2004 | Robergeet et al. ............ 707/101 |
| 6,828,992 | B1 | | 12/2004 | Freeman et al. .............. 345/810 |
| 2004/0078227 | A1 | * | 4/2004 | Morris ............................. 705/2 |
| 2005/0060655 | A1 | | 3/2005 | Gray et al. .................... 715/745 |
| 2005/0076308 | A1 | | 4/2005 | Mansell et al. ............... 715/811 |

* cited by examiner

*Primary Examiner* — Jason B Dunham
*Assistant Examiner* — Amber Altschul

(57) ABSTRACT

A contextually sensitive, user-centric database navigation and accessing software methodology controls navigation through and access to database domains of a medical (e.g., cardiovascular) image and information management system in accordance with the specific role of the user. Being user-centric, rather than patient-centric, the routine is operative to display to a user, upon logging on, a homepage that specifically pertains to the user's area of responsibility, with the information being displayed containing a contextual list of options that are germane to the user's workflow. This facilitates the ability of the user to rapidly navigate through and access one or more data domains specifically relevant to responsibilities and functions of the user, thereby improving the user's efficiency and reducing the time to complete a task.

11 Claims, 23 Drawing Sheets

FIG. 5

PATIENT SEARCH

SELECT ANY OF THE CRITERIA BELOW AND PRESS SEARCH

LAST NAME _____
FIRST NAME _____    MRN _____
DATE OF BIRTH __/__/__   EMPI _____

PROCEDURE TYPE ⇨    PROCEDURE DATE
                    IN THE LAST ___ DAYS
                    IN THE LAST ___ WEEKS
                    ON __/__/__

PRIMARY PHYSICIAN ⇨

REFERRING PHYSICIAN ⇨

[SEARCH]   [CANCEL]

*FIG. 5A*

PHYSICIAN'S VoMN VIEW

[TITAN]
HOME  LOGOFF  CLOSE  USER ROLES  PHYSICIAN

UNREAD STUDIES
DRAG A COLUMN HEADER INTO THE GROUP BY THAT CONFIRM

| FACILITY_ID | ADMIN | CLASSIFIED | FIRST NAME | LAST NAME |
|---|---|---|---|---|
| 00011 | ○ | 2 | ABRAHAM | GREEN |
| 00011 | ○ | 1125 | JAMES | POWER |
| 00011 | ○ | 1455 | KELLY | EWALT |
| 00011 | ○ | 4608 | LOUISE | DENIEC |
| 00011 | ○ | 4608 | HERBERT | KELLEY |
| 00011 | ○ | 4055 | MARK | PUTTNAM |
| 00011 | ○ | 4050 | WILMA | JONES |
| 00011 | ○ | 4030 | LOUISE | WOICK |
| 00011 | ○ | 4034 | JOESPH | PATERNANGE |
| 00011 | ○ | 4036 | WILLIAM | |
| 00011 | ○ | 4038 | WILLIAM | |
| 00011 | ○ | 4632 | | |
| 00011 | ○ | 4634 | | |
| 00011 | ○ | 4636 | SAMUAL | |

VoMN INDICATORS

FINALIZED STUDIES
DRAG A COLUMN HEADER INTO THE GROUP BY THAT CONFIRM

| FACILITY_ID | ADMIN | CLASSIFIED | FIRST NAME | LAST NAME |
|---|---|---|---|---|
| 00011 | ○ | | COLLEEN | WILSON |
| 00011 | ○ | | DORIS | OLIVER |
| 00011 | ○ | | FRED | HOLLMURDA |
| 00011 | ○ | | TEST FIRST NAME | TEST LAST NAME |
| 00011 | ○ | | ROSE | LUAREANO |
| 00011 | ○ | | SHIRELY | FREDDRICK |
| 00011 | ○ | | DOROTHY | ISOSANEN |
| 00011 | ○ | | ELIZABETH | CONWAY |
| 00011 | ○ | | MARY | SYLVIA |
| 00011 | ○ | | BRUCE | BRODDIE |
| 00011 | ○ | | ALICE | ASWAR |
| 00011 | ○ | | JAMES | NAHILL |
| 00011 | ○ | | NORMAN | MAXIM |
| 00011 | ○ | | SAMANTHA | GEN |
| 00011 | ○ | | ELIZABETH | DODGE |
| 00011 | ○ | | RAYMOND | CANNAL |
| 00011 | ○ | | SOCRATES | SIDIROPOLOG |

SEARCH
First name  Day of Birth  Case #
Last Name  MSN
(GO)

(OPEN SEARCH) (CLOSE SEARCH) (CLOSE SEARCH RESULTS)

VERIFICATION OF MEDICAL NECESSITY

VIEW MY PATIENTS

VIEW MY PATIENTS

VIEW MY PATIENTS

USER MESSAGE TO DO

| | SUBJECT | RESOURCE | NOTES | PRIORITY | COMPL |
|---|---|---|---|---|---|
| ☑ | NUCLEAR MED STUDY | DR. BILL | | | |
| ☐ | HOTEL EXAM | DR. DALE | | | |
| ☐ | CT SCAN | DR. BILL | | | |
| ☐ | EP STUDY | DR. CHANDRA | | | |
| ☐ | XR - CHEST | DR. CHANDRA | | | |

FIG. 5C

HOLDING AREA NURSE LOGON SCREEN FIELDS

| PHYSICIAN | LAST NAME | FIRST NAME | SEX | PROCEDURE TYPE | DATE OF BIRTH | MRN | EMPI | OPEN REGISTRY FIELDS |
|---|---|---|---|---|---|---|---|---|
| C. DRAKE | ADAMS | JOHN | M | LHC | 09-02-1940 | 876876 | UYT886 | 101 |
| A. STENT | BAKER | PETE | M | ECHO | 09-04-1953 | 9876t8 | 76ggi6 | n/a |
| B. CURED | HOPKINS | GLADYS | F | ICD IMPLANT | 04-12-1939 | 87876h | 9876hj7 | 24 |

REGISTRY FOR NURSE LOGIN
TITAN FOR CARDIOLOGY
WELCOME JULIA ANDERSON
ANNOTATE STUDY

| REGISTRY | LAST NAME | FIRST NAME | SEX | PROCEDURE | PROC. DATE | BIRTH DATE | MRN | EMPI | OPEN FIELDS |
|---|---|---|---|---|---|---|---|---|---|
| ACC/NCDR | ADAM | JOY | F | CATH | 08-23-2005 | 01-02-1935 | 8Y09877 | 8765654 | 65 |
| ACC/NCD | BAKER | ANDY | M | DX CATH | 08-13-2005 | 04-31-1945 | 087077 | 54e6543 | 42 |
| ACC/PCI | CHARLETON | KEVIN | M | PCI | 08-10-2005 | 12-24-1942 | 7655765 | r876 | 36 |

THIS TABLE IS THE PATIENTS CENSUS LIST. THE PATIENTS ARE ORGANIZED BY REGISTRY, THEN BY PROCEDURE DATE, BUT CAN BE ORDERED BY ANY HEADER BY SIMPLY CLICKING IT. CLICKING AGAIN REORDERS THE PATIENTS IN INVERSE ORDER

REGISTRY NURSE LOGON SCREEN FIELDS

| REGISTRY | LAST NAME | FIRST NAME | SEX | PROCEDURE TYPE | PROC. DATE | DATE OF BIRTH | MRN | EMPI | OPEN REGISTRY FIELDS |
|---|---|---|---|---|---|---|---|---|---|
| ACC/NCDR | ADAMS | JOHN | M | LHC | 08-03-2005 | 09-02-1940 | 876876 | Uyt886 | 101 |
| | BAKER | PETE | M | ECHO | 08-31-2005 | 09-04-1953 | 9876t8 | 76ggi6 | n/a |
| ACC/ICD | HOPKINS | GLADYS | F | ICD IMPLANT | 07-12-2005 | 04-12-1939 | 87876h | 9876hj7 | 24 |

FIG. 12A

VoMN SCREEN FOR CXO

[TITAN]

HOME  LOGOFF  CLOSE   USER ROLES  PHYSICIAN

UNREAD STUDIES

DRAG A COLUMN HEADER INTO THE GROUP BY THAT CONFIRM

| FACILITY_ID | ADMIN | CLASSIFIED | FIRST NAME | LAST NAME |
|---|---|---|---|---|
| 00011 | ☐ | 2 | ABRAHAM | GREEN |
| 00011 | ☐ | 1125 | JAMES | POWER |
| 00011 | ☐ | 11455 | KELLY | EWALT |
| 00011 | ☐ | 4608 | LOUISE | DENIEC |
| 00011 | ☐ | 4608 | HERBERT | KELLEY |
| 00011 | ☐ | 4055 | MARK | PUTTNAM |
| 00011 | ☐ | 4050 | WILMA | JONES |
| 00011 | ☐ | 4030 | LOUISE | WOICK |
| 00011 | ☐ | 4034 | JOESPH | PATERNANGE |
| 00011 | ☐ | 4036 | WILLIAM | MACKINLAY |
| 00011 | ☐ | 4038 | WILLIAM | McCABE |
| 00011 | ☐ | 4632 | OSWALD | SWELL |
| 00011 | ☐ | 4634 | HARRY | BROWN |
| 00011 | ☐ | 4636 | SAMUAL | KASSIE |

FINALIZED STUDIES

DRAG A COLUMN HEADER INTO THE GROUP BY THAT CONFIRM

| FACILITY_ID | ADMIN | CLASSIFIED | FIRST NAME | LAST NAME |
|---|---|---|---|---|
| 00011 | ☐ | | COLLEEN | WILSON |
| 00011 | ☐ | | DORIS | OLIVER |
| 00011 | ☐ | | FRED | HOLLMURDA |
| 00011 | ☐ | | TEST FIRST NAME | TEST LAST NAME |
| 00011 | ☐ | | ROSE | LUAREANO |
| 00011 | ☐ | | SHIRELY | FREDDRICK |
| 00011 | ☐ | | DOROTHY | ISOSANEN |
| 00011 | ☐ | | ELIZABETH | CONWAY |
| 00011 | ☐ | | MARY | SYLVIA |
| 00011 | ☐ | | BRUCE | BRODDIE |
| 00011 | ☐ | | ALICE | ASWAR |
| 00011 | ☐ | | JAMES | NAHILL |
| 00011 | ☐ | | NORMAN | MAXIM |
| 00011 | ☐ | | SAMANTHA | GEN |
| 00011 | ☐ | | ELIZABETH | DODGE |
| 00011 | ☐ | | RAYMOND | CANNAL |
| 00011 | ☐ | | SOCRATES | SIDIROPOLOG |

SEARCH

First name _____  Day of Birth _____  Case # _____

Last Name _____  MSN _____  (GO)

(OPEN SEARCH) (CLOSE SEARCH) (CLOSE SEARCH RESULTS)

VERIFICATION OF MEDICAL NECESSITY

VIEW ALL ☐ PATIENTS ●
VIEW ALL ☐ PATIENTS ○
VIEW ALL ☐ PATIENTS ○

SEARCH   CANCEL

USER MESSAGE TO DO

| | | SUBJECT | RESOURCE | NOTES | PRIORITY | COMPL |
|---|---|---|---|---|---|---|
| ☑ | ☑ | NUCLEAR STUDY | DR. BILL | | ~~HIGHEST~~ | |
| ☑ | ☐ | HOTEL EXAM | DR. DALE | | HIGHEST | |
| ☑ | ☐ | CT SCAN | DR. BILL | | HIGH | |
| ☑ | ☐ | EP STUDY | DR. CHANDRA | | LOW | |
| ☑ | ☐ | XR - CHEST | DR. CHANDRA | | NORMAL | |

*FIG. 13A*

USER-CENTRIC METHODOLOGY FOR NAVIGATING THROUGH AND ACCESSING DATABASES OF MEDICAL INFORMATION MANAGEMENT SYSTEM

CROSS-REFERENCE TO RELATED APPLICATION

The present application claims the benefit of co-pending application Ser. No. 60/700,434, filed Jul. 19, 2005, by John F. Elsholz, entitled: "Mechanism For Verifying And Documenting Necessity Of Performing Medical Procedure And User-Based Tool For Selectively Navigating Through Medical Information Database," assigned to the assignee of the present application and the disclosure of which is incorporated herein.

FIELD OF THE INVENTION

The present invention relates in general to data storage and retrieval systems and user interfaces therefor, and is particularly directed to a contextually sensitive, user-centric methodology that facilitates the ability of a logged-on system user to rapidly navigate through and access one or more data domains of a medical information management system, such as a cardiovascular image and information management system, which data domains specifically pertain to the functions and responsibilities of the user.

BACKGROUND OF THE INVENTION

Today's medical facilities, such as hospitals, that perform procedures such as cardio-related procedures, employ a centralized information storage and management system, in which all information relating to the operation of the hospital and the patients it treats is maintained. Within this overall information storage and management system, there may be contained specific discipline-related information management systems, such as a cardiovascular image and information management system, in which information relating to all cardiology patients, procedures, diagnoses and the like is stored, and may be selectively retrieved by authorized personnel. To date, applications that run on these systems have been organized on the basis of what is commonly referred to as a 'patient'-centric paradigm. As such, whenever any user logs on to a given application, the user's workstation will first display a patient census; then, through the manipulation of various function buttons and icons of the application's graphic user interface, the user may proceed to 'hunt' through the patient list, in an effort to reach a target database from which desired information may be extracted and displayed.

A fundamental drawback to such a patient-centric data retrieval process is the fact that it customarily requires the user to navigate through domains that have absolutely nothing to do with what the user is looking for. A respective user of the system is one to whom specific duties and functions have been assigned; as such, the user is essentially interested only in workflow information which pertains to those functions and duties. For example, a system administrator does not care about finalizing clinical reports, and a registry nurse is not concerned about inventory or scheduling patients. In other words, although it may be necessary for a given user to have access to more than one domain in the system, it is not necessary, nor is it expedient, for each and every user to have access to every domain, such as the patient census, in order for that user to carry out his or her specific function(s).

SUMMARY OF THE INVENTION

In accordance with the present invention, shortcomings of patient-centric data navigation and access schemes, such as, but not limited to, those described above, are effectively obviated by a new and improved contextually sensitive, user-centric database navigation methodology, that controls navigation through and provides access to one or more database domains of a medical information storage and retrieval system, such as a cardiovascular image and information management system, as a non-limiting example, based upon the specific role or function of the user. Being user-centric, rather than patient-centric, means that the methodology of the invention has a priori knowledge of the clinical duties of the user, so that it will automatically open to a workflow homepage that specifically pertains to the clinician's area of responsibility, when he or she logs on to a given application. The information displayed to the user comprises a contextual list of options that are germane to the user's workflow. This facilitates the ability of a logged-on system user to rapidly navigate through and access one or more data domains that are specifically relevant to the responsibilities and functions of the user, thereby improving the user's efficiency and reducing the time to complete a task, as it saves the user keystrokes and time, and effectively eliminates the frustration of trying to navigate through extraneous areas to the right place in the application. In fact, in many instances, the tasks assigned to a given user may not depend on a patient census at all. As will be described, the system administrator will have designated the user's role and permissions when the user was first entered into the system as a new user. Also, the system administrator may add functions to a user's role, that will allow a user to navigate to additional areas of an application, as necessary.

The computer network in which a workstation having access to user-centric information management system navigation and access routine of the present invention provides communication between the workstation and a Hospital Information System (HIS), in which patient-associated information (such as medical history, demographics, insurance information, indicated physical symptoms, etc.) is captured by hospital reception personnel, when a patient is initially checked into the healthcare facility for medical evaluation and treatment. By having access to the HIS, the user-centric information management system navigation and access routine of the present invention is readily able to provide the user with currently available information associated with every patient and any diagnosis or procedure performed.

In addition to providing a link coupled to the HIS, the computer network communicates with diagnostic and test equipment, through which symptomology parameter information of patients, and diagnostic information, that may indicate the need to schedule a procedure, may be obtained. Similarly, once a diagnosis has been completed and a procedure is scheduled, all information relating to the procedure, including the type of procedure, operating physician and attending staff, date of the procedure, the name of the patient on whom the procedure is to be performed, etc. is recorded and stored in the information system.

For purposes of providing illustrative examples of the application of the present description to a variety of respectively different clinical facility functions, the present description will address the manner in which the user-centric methodology of the invention streamlines the ability of a plurality of specifically identified types of users, whose clinical responsibilities are different from one another, to navigate through one or more data domains of a cardiovascular image and information management system. It should be understood, however, that although the invention will be described with respect to its application to the cardiology field, it is applicable to other specialties, such as, but not limited to radiology, oncology, orthopedics, etc.

The respectively different types of users, for whom associated user-centric functions will be described, include, but are not limited to, a physician, a holding area nurse, a clinician (lab tech), a scheduler, an Information Technologist or Chief Information Officer, a system administrator, a department administrator, a registry nurse, and a chief executive of the medical facility. The basic functions which may be generally performed by respectively different ones of the users include but are not limited to: scheduling; generating reports (clinical, administrative, financial); statistics (charge capture, Morbidity/Mortality reports, departmental supplies utilization, etc.); broken study tools; patient locator/search tools; registries/research datapoints; system status monitoring; and audit logs. The specific functions performed by each of the different classes of users will be detailed in the course of descriptions of workflow diagrams for those users. When a specific function is invoked, the user is then guided through one or more associated screens, that allow rapid navigation through databases, information contained within which the user may require to complete a given task.

When a user logs in to the system, via the manipulation of one or more buttons of a logon screen, a subroutine associated with that particular class of user will cause the user's workstation to automatically display a workflow homepage for that user. The system administrator will have designated the user's role and permissions when the user was first entered into the system as a new user. This a priori known role or class of the logged-on user serves to automatically display the appropriate workflow homepage screen for the user, which contains the roles or functions of a specific class of user, the tasks which that user performs in the discharge of his/her duties, and the features and functions in the application that relate to that particular user's respective needs.

BRIEF DESCRIPTION OF THE DRAWINGS

FIG. 5 shows an example of a physician's graphic user interface that may be displayed on the physician's workstation, in the course of navigating through one or more functions of the workflow diagram of a physician's workflow homepage of FIG. 4;

FIG. 5A shows an example of a screen displaying patient search information;

FIG. 5C shows an example of a screen displaying a physician's VOMN view;

FIG. 6A shows an example of holding area nurse logon screen fields;

FIG. 12 shows the logon screen as displayed on a workstation of a user of a cardiovascular image and information management system, that employs the contextually sensitive, user-centric based navigation mechanism of the present invention, where the user logged into the system is a registry nurse;

FIG. 12A shows an enlargement of the examples of screen fields of the logon screen of FIG. 12;

FIG. 13A shows an example of a VOMN screen for a CXO.

DETAILED DESCRIPTION

Figure 1:
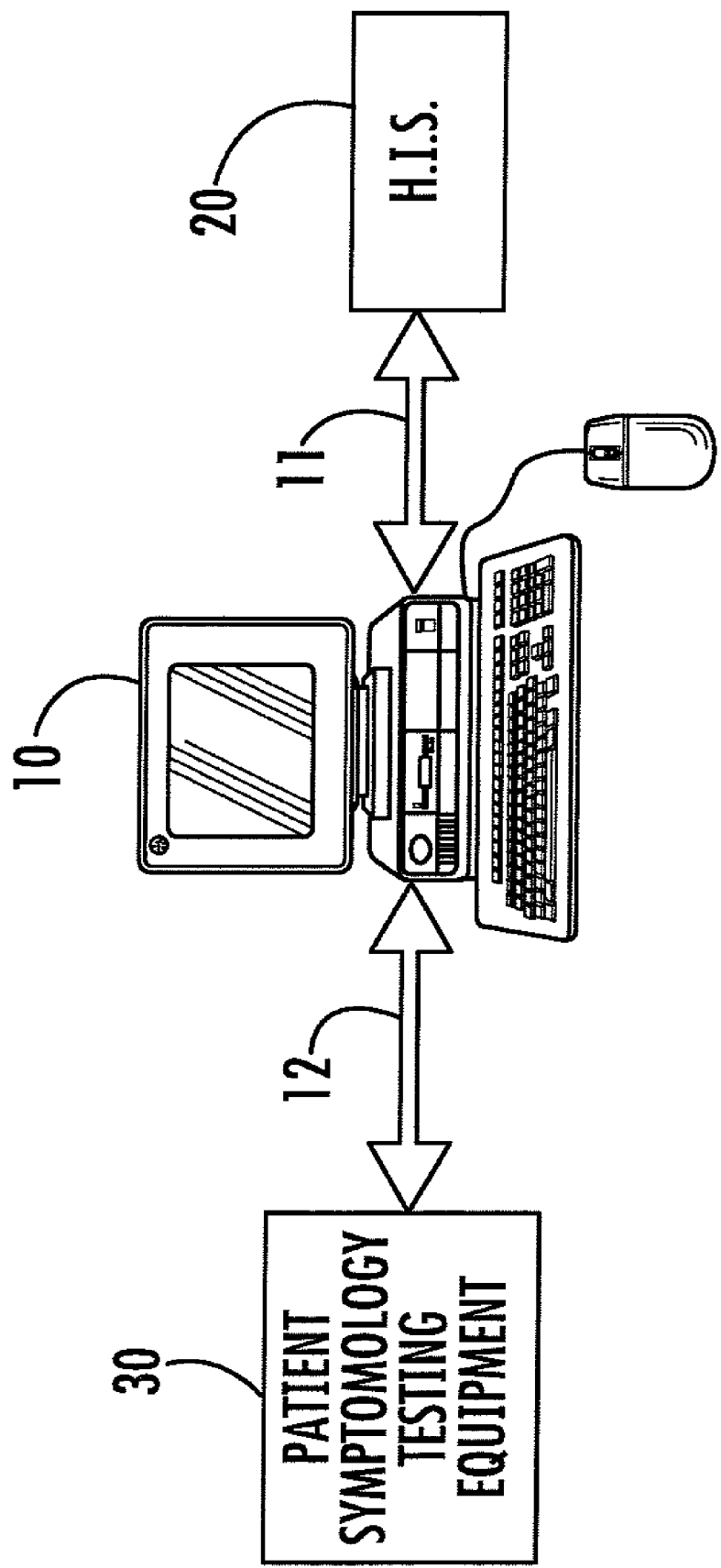
FIG. 1 is a reduced complexity block diagram illustration of a typical computer network, such as may be installed at a facility of a healthcare provider (e.g., hospital), in which the contextually sensitive, user-centric based methodology of the present invention, for navigating through and access data domains of a medical information management system, may be employed.

Before describing the user-centric based methodology of the present invention for navigating through and accessing data domains of a medical information management system, such as, but not necessarily limited to, a cardiovascular image and information management system, it should be observed that the invention resides primarily in a set of contextually sensitive, user workflow and database search and retrieval software, that may be loaded into and executed on a conventional computer (e.g., laptop, desktop, server, and the like), plus associated graphic user interfaces, through which the software is controlled, with results of the execution of various subroutines of the software being displayed to a user of the system. Consequently, the configuration of the system and the manner in which it may be interfaced with conventional healthcare service provider data storage and processing systems, such as a Hospital Information System (HIS), and equipments employed by the health facility to test and gather symptomatic parameter information on patients have, for the most part, been depicted in the drawings by readily understandable functional block diagrams, and user interface display screens that display user function-associated menus and user workflow diagrams, which show only those specific aspects that are pertinent to the methodology of the present invention, so as not to obscure the disclosure with details which will be readily apparent to those skilled in the art having the benefit of the description herein. Thus, the block diagram and associated graphic user interface and user workflow diagrams are primarily intended to show the major components of a preferred embodiment of the invention in convenient functional groupings, whereby the present invention may be more readily understood.

Moreover, it is to be understood that the methodology of the present invention is applicable to expeditiously navigating through and retrieving a wide variety of information stored in one or more database domains of a medical service facility's information management system, and thus is not intended to be limited in its scope. For purposes of providing a non-limiting, but illustrative, example of its use, the following description will address the application of the invention to navigating through and retrieving information stored within a cardiovascular image and information management system by a plurality of users, whose functions and responsibilities are different from one another, and therefore require access to respectively different workflow-related domains of the information management system, in the course of carrying out their assigned tasks. As pointed out above, although the invention will be described with respect to its application to a cardiology related image and information management system, it is to be understood that it is applicable to other specialties, such as, but not limited to radiology, oncology, orthopedics, etc.

Attention is initially directed to FIG. 1, which is a reduced complexity block diagram illustration of a computer network, such as may be installed at a facility of a healthcare provider (e.g., hospital), in which the present invention may be employed. As shown therein, the service provider computer network includes a desktop computer or workstation 10, in which the user-centric database navigation and data retrieval software of the present invention has been installed, and through which healthcare facility personnel are able to navigate among respective displayed windows of a graphics user interface and retrieve data, as necessary, in association with their predefined responsibilities and duties that require access to the network.

The computer network in which the workstation 10 is installed includes a link 11 between the workstation and a Hospital Information System (HIS) 20, in which patient-associated information (such as medical history, demographics, insurance information, indicated physical symptoms (such as crushing chest pain, dizziness, fainting, chest palpitations), etc.) is captured by hospital reception personnel, when a patient is initially checked into the healthcare facility for medical evaluation and treatment. By having access to the HIS 20, the user-centric information management system navigation and access routine of the present invention is readily able to provide the user with currently available information associated with every patient and any diagnosis or procedure performed.

In addition to providing a link coupled to the HIS 20, the computer network includes a link 12 to diagnostic and test equipment 30, through which symptomology parameter information of patients, and diagnostic information, that may indicate the need to schedule a procedure, may be obtained. Similarly, once a diagnosis has been completed and a procedure is scheduled, relevant information relating to the procedure, including the type of procedure, operating physician and attending staff, date of the procedure, the name of the patient on whom the procedure is to be performed, etc. is recorded and stored in the HIS.

Figure 2:
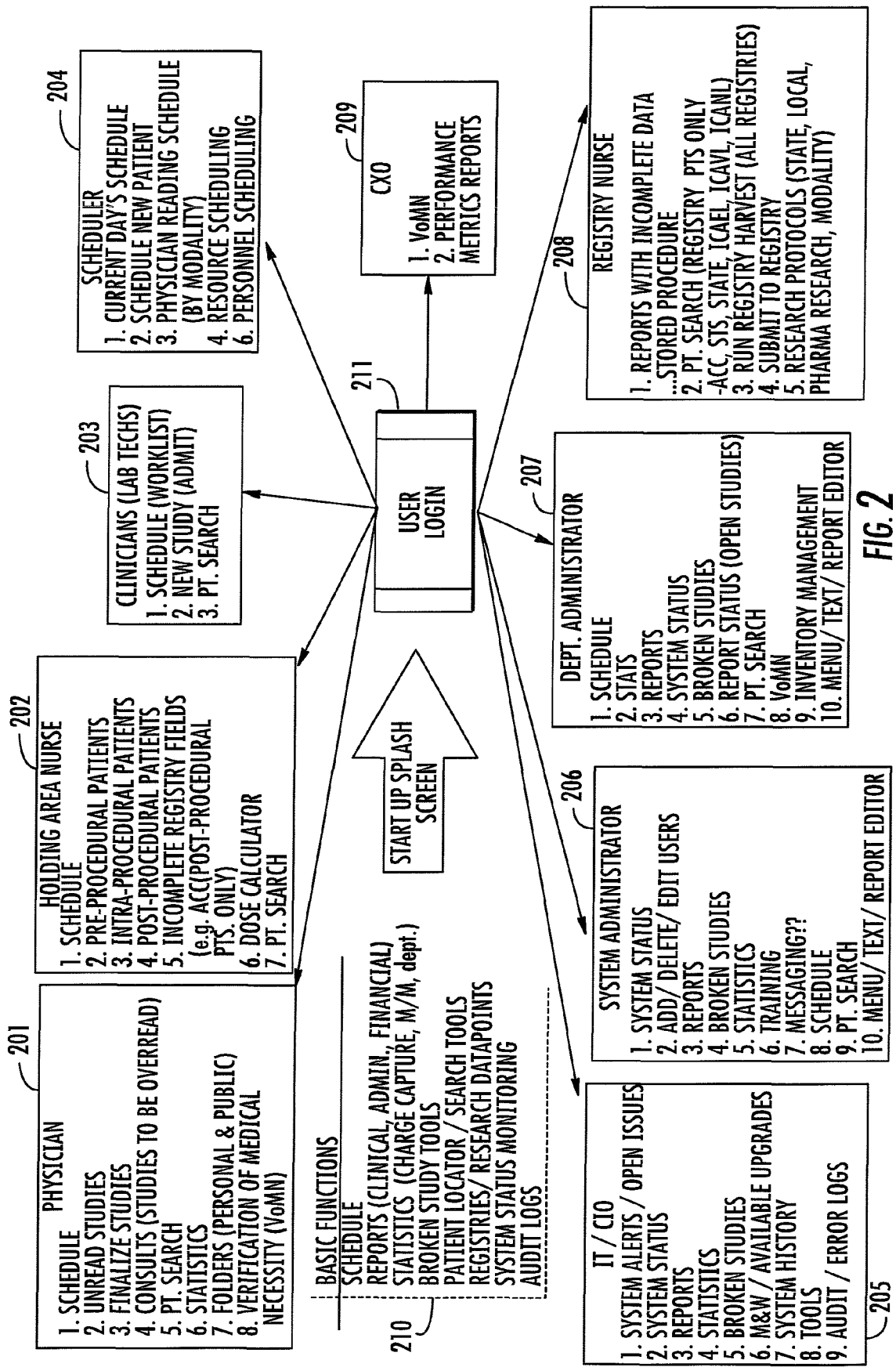
FIG. 2 diagrammatically shows a set of nine different classes of users of a cardiovascular image and information management system, in which the contextually sensitive, user-centric based-methodology of the present invention has been installed.

As noted above, for purposes of providing non-limiting, but illustrative examples of the application of the present description to a variety of respectively different clinical facility functions, the present description will address the manner in which the user-centric database navigation methodology of the invention streamlines the ability of a plurality of specifically identified types of users, whose clinical responsibilities are different from one another, to navigate through one or more domains of a cardiovascular image and information management system. To this end, as an illustrative example, FIG. 2 diagrammatically shows a set of nine different classes of users of the system and a listing for each user of some of their individual job functions. The users include a physician 201, a holding area nurse 202, a clinician (lab tech) 203, a scheduler 204, an Information Technologist or Chief Information Officer 205, a system administrator 206, a department administrator 207, a registry nurse 208, and a senior executive of the hospital (CXO) 209.

Also shown in FIG. 2 is a generic function block 210, that lists a set of basic functions which may be generally performed by respectively different ones of the users 201-209. These include: scheduling; generating reports (clinical, administrative, financial); statistics (charge capture, (see above clarifications) M/M, dept.); broken study tools; patient locator/search tools; registries/research datapoints; system status monitoring; and audit logs. The specific functions listed for each of the users 201-209 in FIG. 2 will be referenced in the course of descriptions of workflow diagrams for those users, depicted in FIGS. 4, and 6-13, to be described. FIG. 2 further shows a user login function 211, which, by virtue of the fact that the present invention is user-centric, is operative to automatically call up and display the functions listed for the particular one of the users 201-209, as represented by the respective arrows emanating from the user login block 211 to the user blocks 201-209, when that user logs on to the system.

Figure 3:
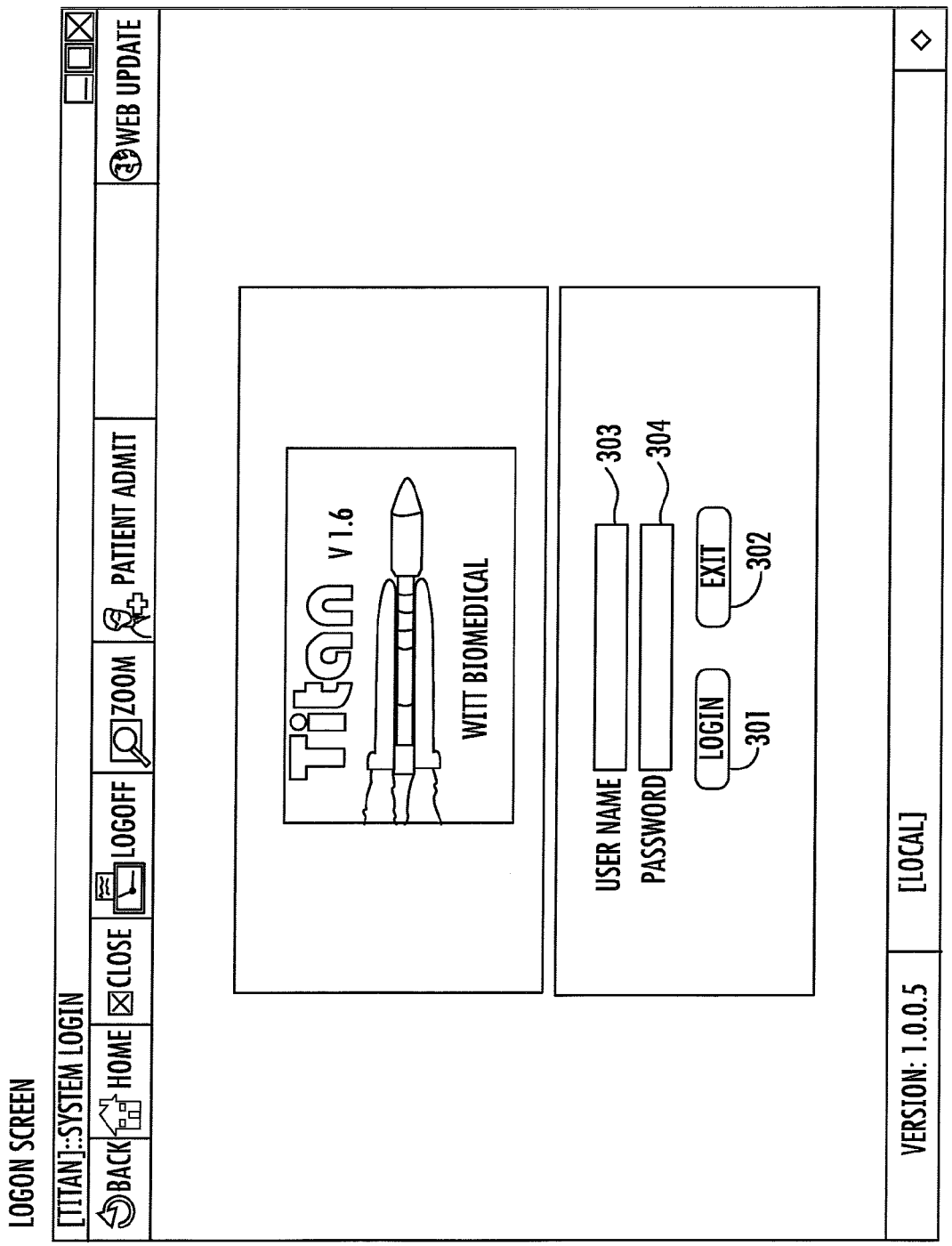
FIG. 3 shows a logon screen as displayed on a workstation of a user of a cardiovascular image and information management system, that employs the contextually sensitive, user-centric based navigation mechanism of the present invention.

The user login block 211 of FIG. 2 is more particularly depicted in the illustration of the graphic user interface of FIG. 3, which shows respective components that are displayed by a logon screen on the user's workstation. The logon screen of FIG. 3 is shown as containing a login button 301, and exit button 302 and traditional user name and password fields 303 and 304, respectively. As pointed out above, the system administrator will have designated the user's role and permissions when the user was first entered into the system as a new user. This a priori known role of the logged-on user serves to automatically display the appropriate workflow-displaying homepage screen for the user, as will be described.

Figure 4:
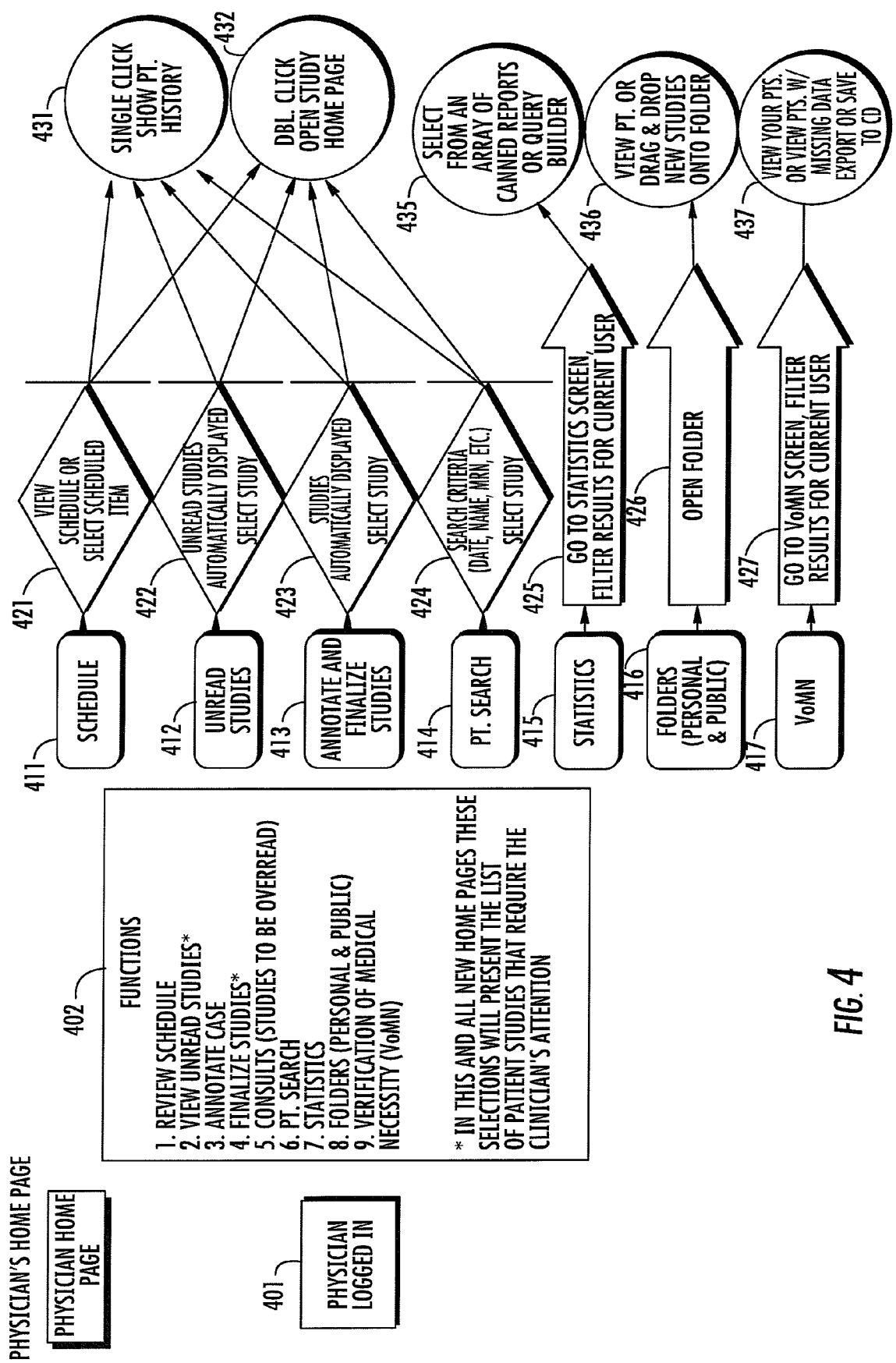
FIG. 4 shows the workflow homepage as displayed on a workstation of a user of a cardiovascular image and information management system, that employs the contextually sensitive, user-centric based navigation mechanism of the present invention, where the user logged into the system is a physician/cardiologist.

FIG. 4 shows the homepage that is displayed by the workstation's display screen, for the case that the user logged into the system is a physician/cardiologist (shown at 401), whose functions include those listed in block 201 in FIG. 2, described above, and repeated in the function block 402 in FIG. 4. The workflow diagram of FIG. 4, as well as those subsequently described, graphically illustrates the roles or functions of a specific type of user, the tasks which that user performs in the discharge of his/her duties, and the features and functions in the application that relate to that particular user's respective needs. FIG. 4 contains a workflow diagram that has commonality for both an interventional cardiologist and a non-interventional cardiologist.

Non-interventional cardiologists include physicians who perform echocardiology studies, nuclear medicine studies, non-invasive peripheral vascular examinations, and doctors who read EKG and holter exams. This type of physician often sits at a desk and uses a worklist to maximize his/her efficiency during the day. In other words, the non-interventional cardiologist can be expected to sit at a computer workstation, and read/interpret examination reports that have been prepared for them by technicians or interns in residence. Interventional physicians, on the other hand, are not worklist-driven, but move from one procedure to the next, and having to complete procedural reports rapidly before the next case starts. In spite of these differences, these two types of physicians have commonalities in their individual routines or functions, as depicted in FIG. 4. These tasks include scheduling 411, unread studies 412, annotating and finalizing studies 413, patient searching 414, reviewing statistics 415, reviewing contents of folders (personal and public) 416, and verification of medical necessity (VOMN) 417.

By invoking the schedule function 411, the physician may view a schedule or select a schedule item, as shown at 421. From the schedule function 421, the physician may proceed to call up a screen showing patient history, via a single click on the displayed patient name, as shown at 431, or double click to open a study home page, as shown at 432. Invoking the unread studies function 412 causes a list of unread studies to be automatically displayed, and the physician may select from the displayed list, as shown at 422. Again, the physician may suitably single or double click to state 431 or state 432. By invoking the annotate and finalize studies function 413, the physician may have the studies automatically displayed for selection as shown at 423, from which the physician may selectively single or double click to state 431 or state 432. Invoking the patient search function 414 provides the physician with a patient list and displayed search criteria from which the physician may select for study, as shown at 424. Again, the physician may suitably single or double click to state 431 or state 432.

For the statistics function shown at 415, the work flow proceeds to the statistics screen and filters the results for the currently logged-on physician, as shown at 425, and allows the physician to select from an array of stored reports or to query the builder, as shown at state 435. For the folders function at 416, the work flow proceeds to open a selected folder at 426, and allows the physician to view a patient folder or drag and drop new studies into the folder, as shown at state 436.

The last listed function, verification of medical necessity, shown at 417, involves an automated software routine that enables the user to readily capture and archive, in an audit file, patient and clinical information, that is effective to verify—comply with guidelines promulgated by the Center for Medicare/Medicaid Services (CMS) for—the medical necessity of performing a given medical procedure, and thereby ensure that the healthcare service provider and the physician will be properly reimbursed for the costs of performing the procedure and will be able to readily pass a CMS audit of its facility and associated medical personnel (physicians). Such a routine is preferably of the type described in U.S. patent application Ser. No. 11/273,790, published as U.S. Patent Application Publication No. 2007/0021977, filed on Nov. 15, 2005, by John F. Elsholz, entitled: "Automated System For Capturing And Archiving Information To Verify Medical Necessity Of Performing Medical Procedure," assigned to the assignee of the present application and the disclosure of which is incorporated herein.

Briefly, in accordance with the invention described in that application, if the compilation of information regarding a patient and procedure reveals that the audit file lacks one or more pieces of information to satisfy medical necessity requirements, the inventive system will visually alert medical personnel to the extent of the shortcoming and specifically tag what is lacking. This will allow the system user to activate one or more objects of a user interface to initiate a search of available resources that contain the required information, or to manually enter the information into the system, so that the audit file may be completely filled in with whatever information is missing. Once the audit file complies with CMS requirements, the system will alert medical personnel to that fact by a colored (e.g. green) alert indicator of the workstation display screen.

When the VOMN function 417 is invoked, the work flow proceeds to the VOMN screen, an example of which is shown in FIG. 5C, and filters the results for the currently logged-on user, as shown at 427, so that the physician may view his/her patient data, or view patients having missing data, so that any missing data may be accessed and stored pursuant to the functionality of the VOMN routine, and then allow the VOMN data to be exported or saved to an auxiliary storage, such as a compact disc, as shown at 437.

Figure 5:
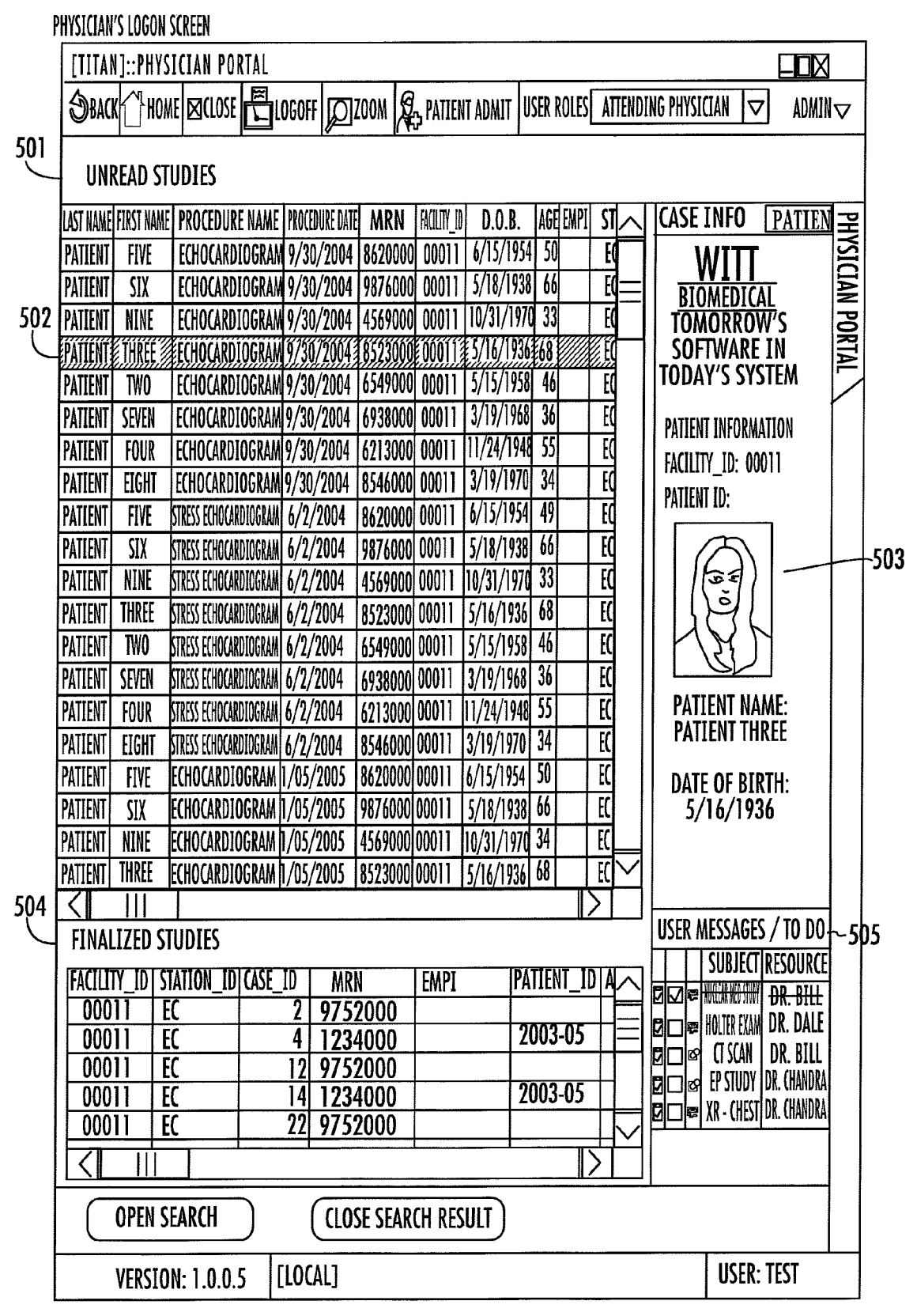

FIG. 5 shows an example of a physician's logon screen that may be displayed on the physician's workstation, in the course of the physician navigating through one or more functions of the workflow diagram of the physician's homepage screen of FIG. 4. As shown in FIG. 5, for unread studies 501, a selected patient has been highlighted at 502 by the physician, so that the physician may document the case currently in progress; also displayed are a "patient information" field 503, a "finalize studies" field 504, and a "user messages/to do" field 505. As described above, any of these or other displayed functions may be readily performed by the physician with a single mouse click after logging on.

Figure 5B:
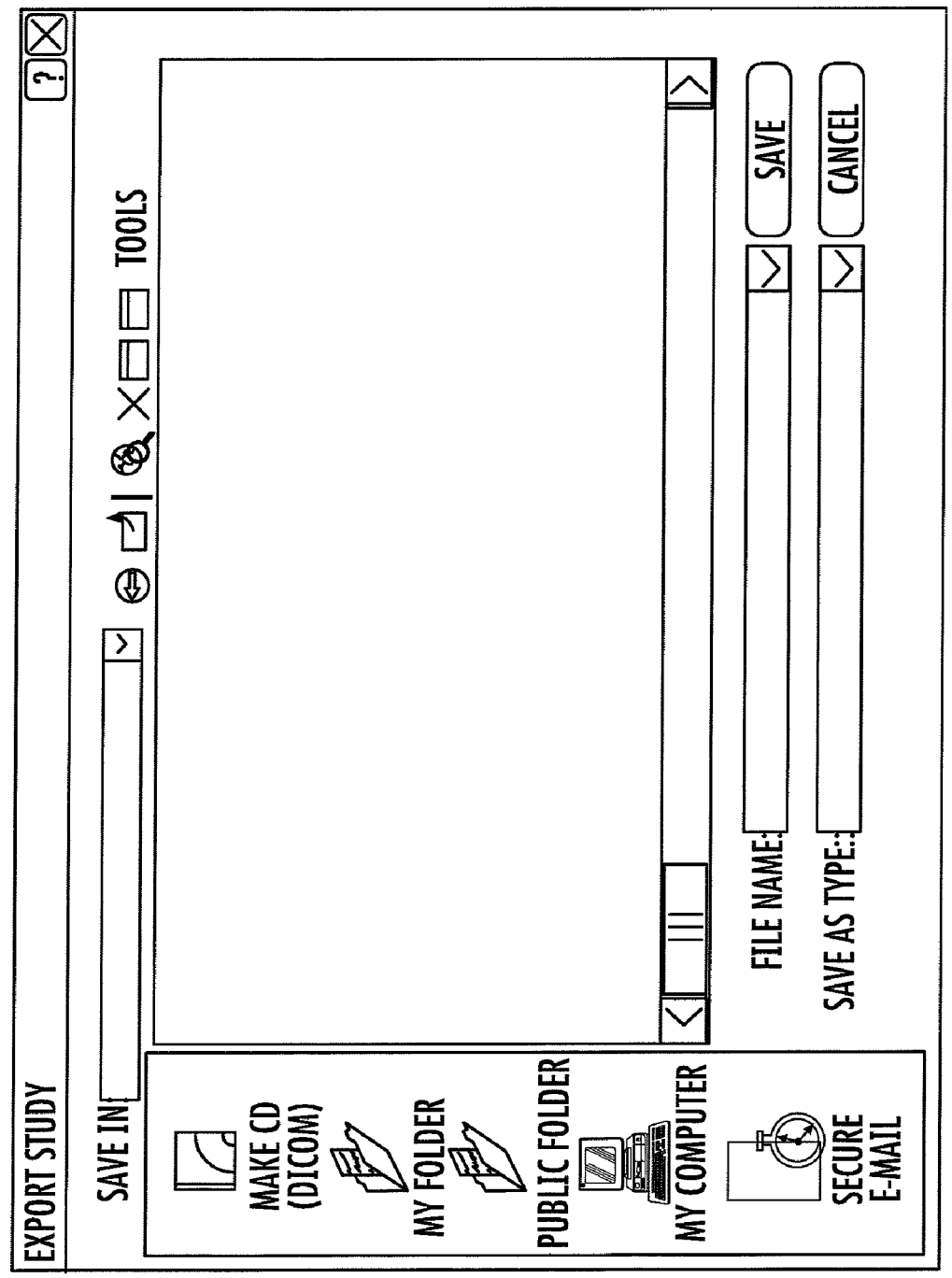
FIG. 5B shows an example of a screen displaying export study information.

FIG. 5A shows an example of a screen displaying patient search information, such as may be generated when invoking the patient search function at 414, while FIG. 5B shows an example of a screen displaying export study information, such as may be generated in the course of saving the results of a finalized study.

Figure 6:
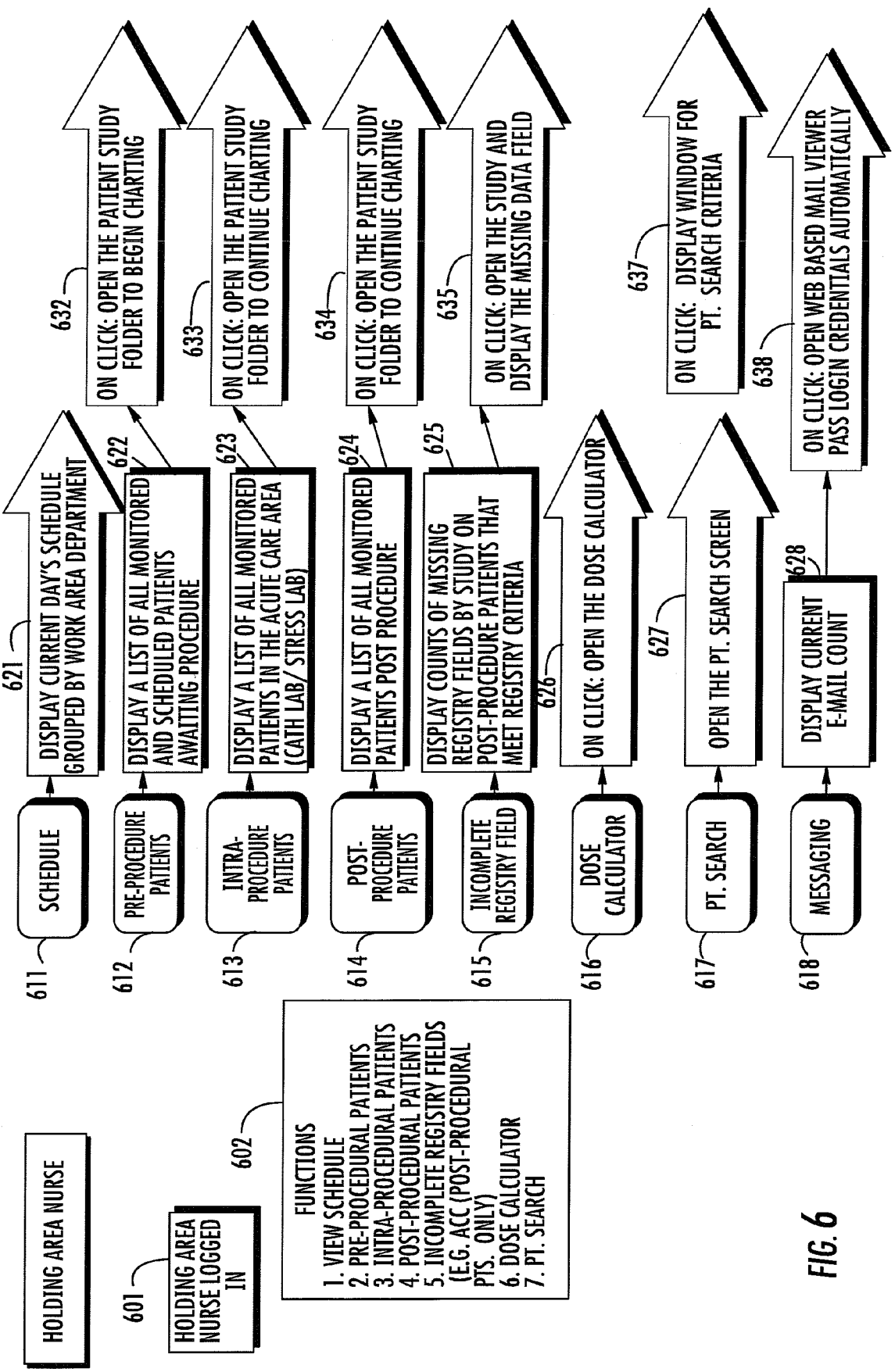
FIG. 6 shows the workflow homepage as displayed on a workstation of a user of a cardiovascular image and information management system, that employs the contextually sensitive, user-centric based navigation mechanism of the present invention, where the user logged into the system is a holding area nurse.

FIG. 6 shows the homepage that is displayed by the workstation's display screen, where the user logged into the system is a holding area nurse (shown at 601), whose functions include those listed in block 202 in FIG. 2, described above, and repeated in the function block 602 in FIG. 6. FIG. 6A shows various examples of screen fields of a holding area nurse's logon screen. A holding area nurse is involved with patients in catheterization (cath), echo, electrophysiology (EP), peripheral vascular (PV) and nuclear medicine labs, who are prepared for a procedure in a holding area. This is especially true for cath and EP labs, where the patient is received, shaved, prepped, sedated, and IVs are inserted pre-procedurally, and where arterial hemostasis occurs post-procedurally. Holding nurses must chart the patient, assess the patient on Aldrete or ASA scores, and report the patient's conscious sedation under mandate of many state laws. As shown in FIG. 6, the functions that may be performed by a holding nurse include scheduling 611, pre-procedural charting of patients 612, intra-procedural charting of patients 613, post-procedural charting of patients 614, checking whether there are any incomplete registry fields 615, dosage calculation 616, patient search 617, and messaging 618.

When the scheduling function 611 is invoked, the current day's schedule, grouped by work area/department, for the logged-on holding nurse, is called up and displayed on the holding nurse's workstation's display screen, as shown at 621. Invoking the pre-proceduring patients function 612 causes a list of all monitored and scheduled patients awaiting a procedure to be displayed, as shown at 622. By clicking on a particular patient in the list, the holding nurse may open that patient's study folder to begin charting, as shown at 632. Invoking the intra-proceduring patients function 613 causes a list of all monitored patients in the acute care area (Cath/EP/PV/Stress Labs) to be displayed, as shown at 623. By clicking on a particular patient in the list, the holding nurse may open that patient's study folder to continue charting, as shown at 633. Invoking the post-proceduring patients function 614 causes a list of all monitored patients post procedure to be displayed, as shown at 624. By clicking on a particular patient in the list, the holding nurse may open that patient's study folder to continue charting, as shown at 634.

When the incomplete registry fields function 615 is invoked, counts of missing registry fields by study, on post procedure patients that meet registry criteria are displayed, as shown at 625. Clicking on a particular study opens the study and displays the missing data fields, as shown at 635. Invoking the dose calculator function 616 is accomplished by clicking on a dose calculator button, which opens the dose calculator, as shown at 626. Invoking the patient search function 617 opens the patient search screen, as shown at 627. Clicking on this screen then displays a window for patient search criteria, as shown at 637. The last function, which is optional, is a messaging function 618. If employed, then when invoked, it will cause the current e-mail count to be displayed, as shown at 628. The holding nurse may then proceed to click on the e-mail open button, to open the web based mail viewer, which causes login credentials to be supplied automatically, as shown at 638.

Figure 7:
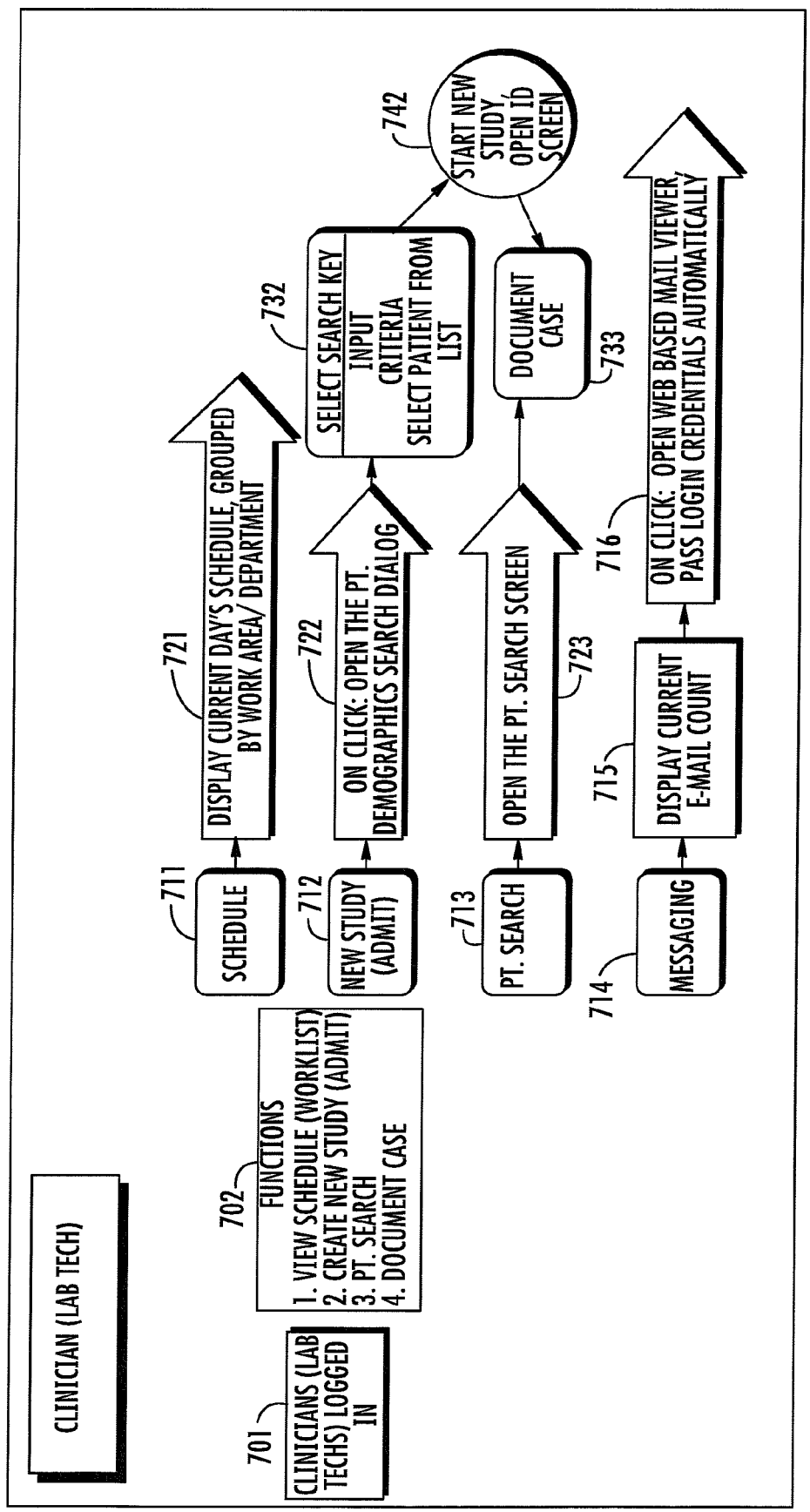
FIG. 7 shows the workflow homepage as displayed on a workstation of a user of a cardiovascular image and information management system, that employs the contextually sensitive, user-centric based navigation mechanism of the present invention, where the user logged into the system is a clinician (laboratory technician)

FIG. 7 shows the workflow homepage that is displayed by the workstation's display screen, where the user logged into the system is a clinician or lab tech (shown at 701), whose functions include those listed in block 203 in FIG. 2, described above, and repeated in the function block 702 in FIG. 7. The primary task of procedural documentation during a cardiac catheterization, echocardiology, electrophysiology, vascular or nuclear medicine exam falls to the lab technicians who, along with the nurses, are the workhorses in the patient charting world. Physicians always review their notes, add findings, complications, and interpretations, but the lab techs perform an indispensable and vital documentation function.

As shown in FIG. 7, the functions that may be performed by a lab technician include scheduling 711, new study (admitting) 712, patient search 713, and messaging 714. When the scheduling function 711 is invoked, the current day's schedule, grouped by work area/department/physician, for the logged-on clinician, is called up and displayed on the lab tech's workstation, as shown at 721. Invoking the new study function 712, by clicking on a new study button, opens the patients' demographics search dialog, as shown at 722. The user may then select a search key, as shown at 732, and supply search criteria and select a patient from a displayed list. The user then proceeds to state 742, to start a new study, and open an ID screen. The case is then documented at 733. Invoking the patient search function 713 opens the patient search screen, as shown at 723. The case is then documented at 733. The last function is an optional messaging function 714. If included, then when invoked, it will cause the current e-mail count to be displayed, as shown at 715. The lab tech may then proceed to click on the e-mail open button, so open the web based mail viewer, which causes login credentials to be supplied automatically, as shown at 716.

Figure 8:
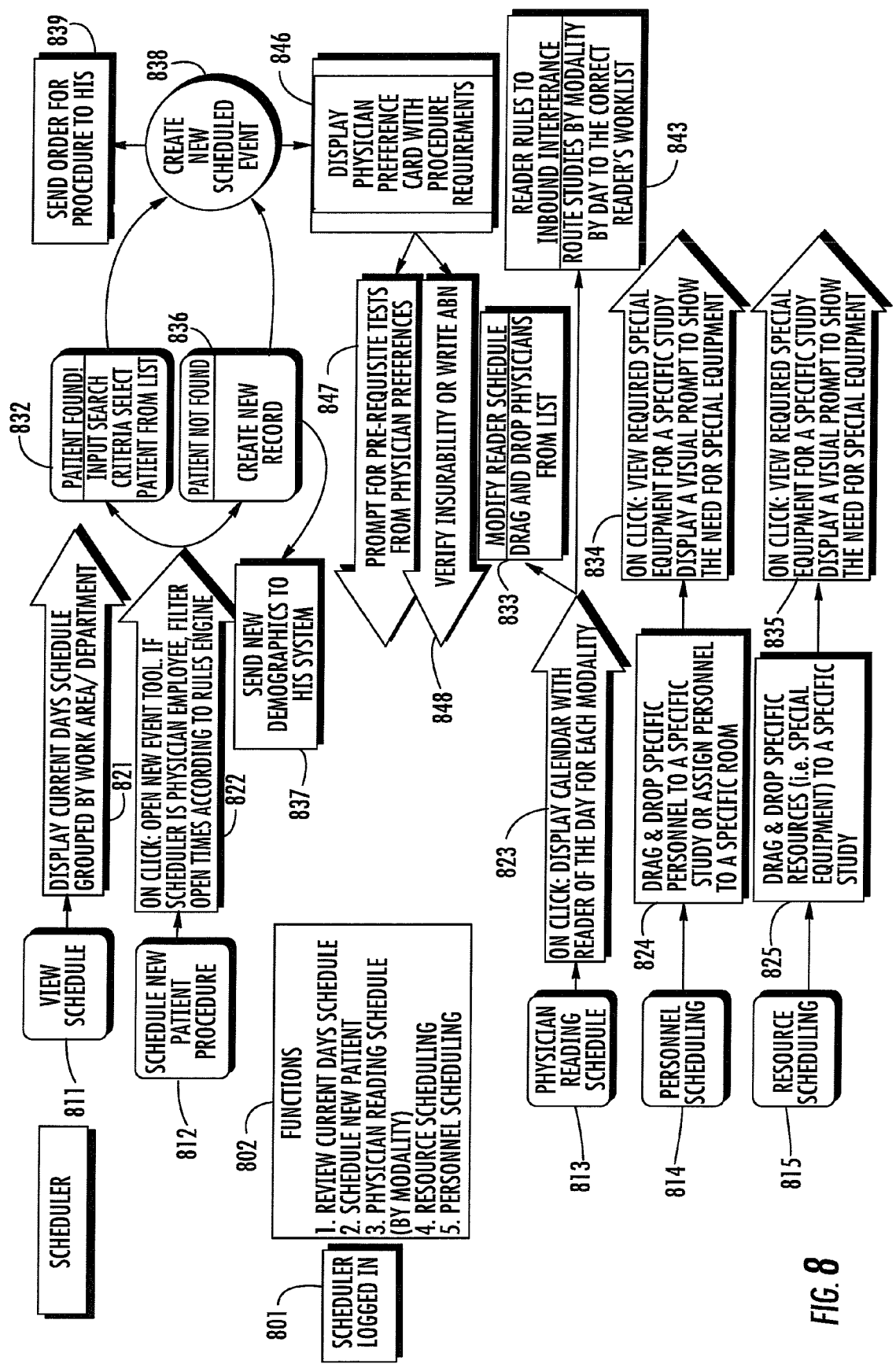
FIG. 8 shows the workflow homepage as displayed on a workstation of a user of a cardiovascular image and information management system, that employs the contextually sensitive, user-centric based navigation mechanism of the present invention, where the user logged into the system is a scheduler.

FIG. 8 shows the workflow homepage that is displayed by the workstation's display screen, where the user logged into the system is a scheduler (shown at 801), whose functions include those listed in block 204 in FIG. 2, described above, and repeated in the function block 802 in FIG. 8. The first point of entry with any procedure is getting it scheduled in the system. The scheduler may be in the hospital, a unit, or in a remote setting, such as a doctor's office. To allow for remote access, the user-centric methodology of the invention employs web-based communications, thereby allowing a physician's office nurse to log on remotely, find an opening in the schedule, and schedule the physician and the patient for the case. For this purpose, as shown in FIG. 8, functions that may be performed by a scheduler include viewing the schedule 811, scheduling a new patient procedure 812, having the physician read the schedule 813, personnel scheduling 814, and resource scheduling 815.

When the view schedule function 811 is invoked, the current day's schedule, grouped by work area/department/physician, for the logged-on scheduler, is called up and displayed on the scheduler's workstation, as shown at 821. To schedule a new patient procedure (function 812), the scheduler clicks on the displayed function, to open a new event tool. If the scheduler is a physician's employee, the available time slots in the schedule are filtered according to a prescribed rules engine, as shown at 822. The identity of the patient may be located from a patient list, based on input search criteria; where the patient is found in the list, the workflow moves to state 832—patient found. Where the patient is not found in the patient list, a new record is created at state 836, and the patient's demographic data is forwarded to the Hospital Information System (HIS) to update the HIS database, at state 837. Given the patient's identity, from states 832 or 836, a new scheduled event is created at 838, and an order for the procedure is sent to the HIS, at 839. In addition, the physician's preference card with procedure requirements is displayed, at state 846. This generates a prompt for pre-requisite tests from the physician's preferences, at 847. In addition, the scheduler is instructed to verify insurability or to write an Advance Beneficiary Notice at 848 so the patient can arrange financing to pay for the procedure.

When the physician's reading schedule function 813 is invoked, a calendar with the reader of the day for each modality is displayed by an on-click, as shown at 823. The reader's schedule may be modified at 833, by using the workstation's mouse to drag and drop physicians from the displayed list.

Also, at state 843, reader rules are supplied to inbound interfaces, and studies are routed by modality, and by day to the correct reader's worklist. When the personnel scheduling function 814 is invoked, the user may drag and drop specific personnel to a specific study or assign personnel to a specific room, as shown at state 824. The user may then click on a specific study to view whether any special equipment is required, as shown at 834. If special equipment is required, the user invokes an icon to provide a visual prompt to show such a need. For resource scheduling (function 815), the scheduler may drag and drop resources (e.g., special equipment) to a specific study, as shown at 825. The user may then click on a specific study to view whether any special equipment is required, as shown at 835 and, if special equipment is required, the user invokes an icon to provide a visual prompt to show such a need.

Figure 9:
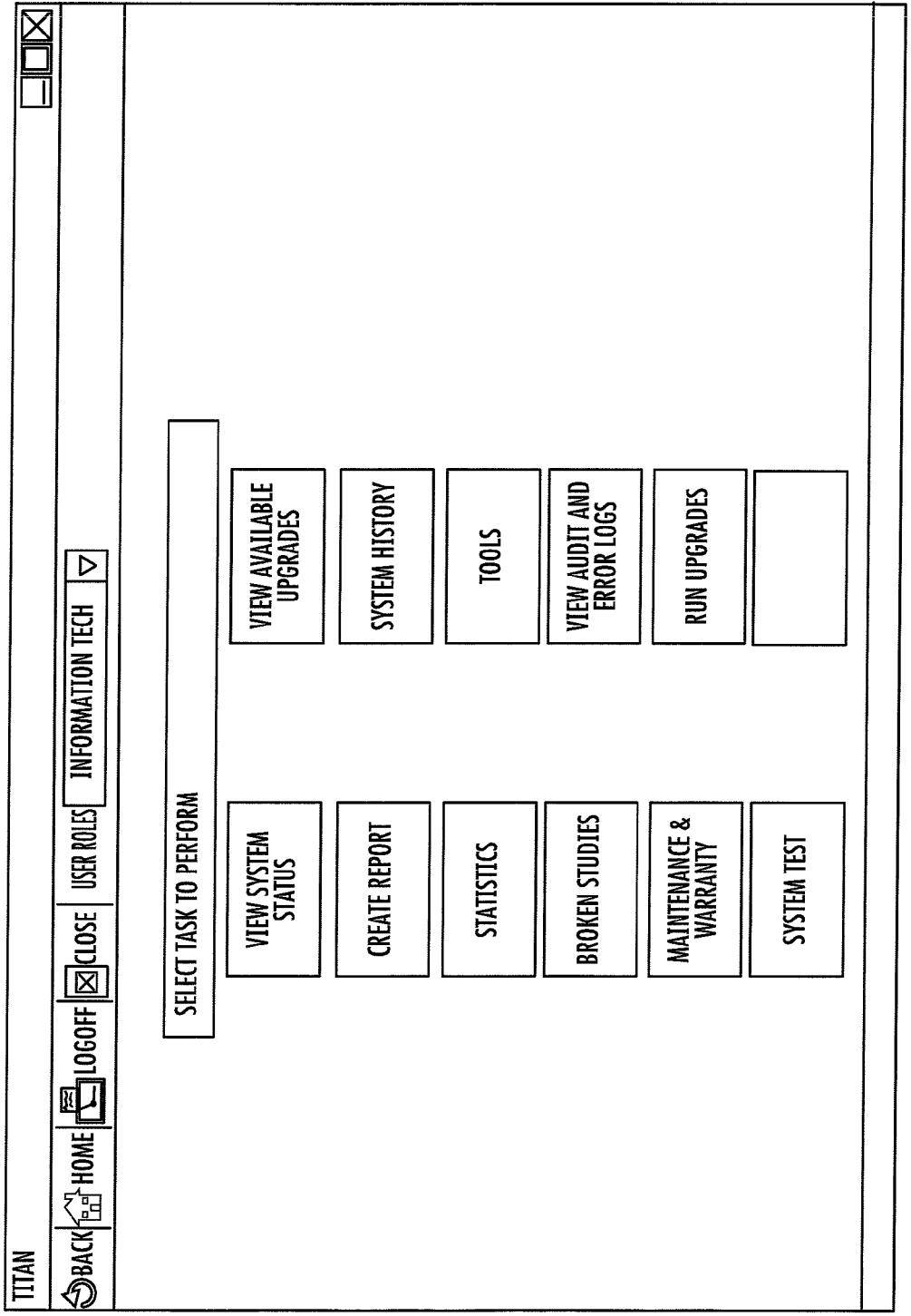
FIG. 9 shows an IT logon screen as displayed on a workstation of a user of a cardiovascular image and information management system, that employs the contextually sensitive, user-centric based navigation mechanism of the present invention, where the user logged into the system is an Information Technologist (IT) or Chief Information Officer (CIO)
Figure 9A:
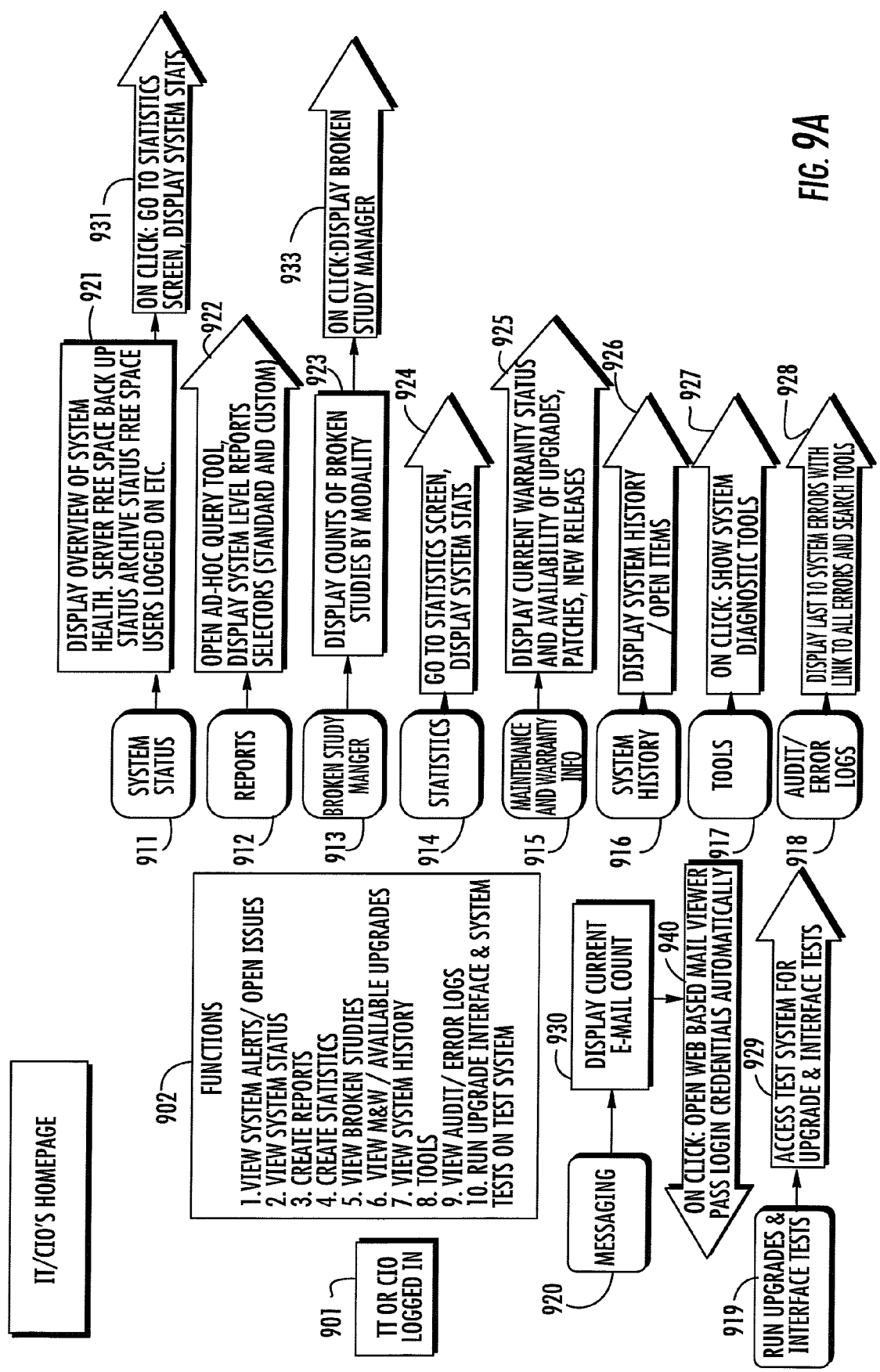
FIG. 9A shows the workflow of an IT/CIO user associated with FIG. 9.

FIG. 9 shows the IT logon screen that is displayed by the workstation's display screen, while FIG. 9A shows the associated workflow, where the user logged into the system is an information technologist (IT) or CIO (shown at 901), whose functions include those listed in block 205 in FIG. 2, described above, and repeated in the function block 902 in FIG. 9A. The burden of supporting and maintaining the system falls to the information technologist, and eventually to the CIO, who has ultimate responsibility for the compatibility of all systems. The functions of FIGS. 9 and 9A include diagnostic and monitoring tools that specifically address the needs of the IT staff to support and monitor the system.

More particularly, functions that may be performed by an IT/CIO include a system status check 911, reports 912, a broken study manager 913, statistics 914, maintenance and warranty info 915, system history 916, tools 917, audit/error logs 918, running upgrades and interface tests 919, and messaging 920. Invoking the system status function 911 calls up and displays an overview of system health, including parameters that include server free space, back-up status, archive status, free space, users logged on, and the like, as shown at 921. The user may then click on the statistics screen and display system statistics or generate statistical reports, as shown at 931.

The report function 912 involves opening an ad-hoc query tool, and the display of system level reports selectors (standard and custom), as shown at 922. When the broken study manager 913 function is invoked, counts of broken studies are displayed according to modality, as shown at 923. Via an on click the broken study manager may then be displayed, as shown at 933. When the statistics function 914 is invoked, the statistics screen is called up and displayed as shown at 924. Invoking the maintenance and warranty information function 915 displays current warranty status and availability of upgrades, patches, new releases, as shown at 925.

Invoking the system history function 916 displays system history and open items, as shown at 926. Clicking on the tools function 917, brings up a list of system diagnostic tools, as shown at 927. When the audit/error logs function 918 is invoked, the last ten system errors are displayed, together with a link to all errors and search tools, as shown at 928. Invoking the run upgrades and interface test function 919 accesses the test system for upgrade and interface tests, as shown at 929. Invoking an optional messaging function 920, if employed, causes the current e-mail count to be displayed, as shown at 930. The IT/CIO may then proceed to click on the e-mail open button, so open the web based mail viewer, which causes login credentials to be supplied automatically, as shown at 940.

Figure 10:
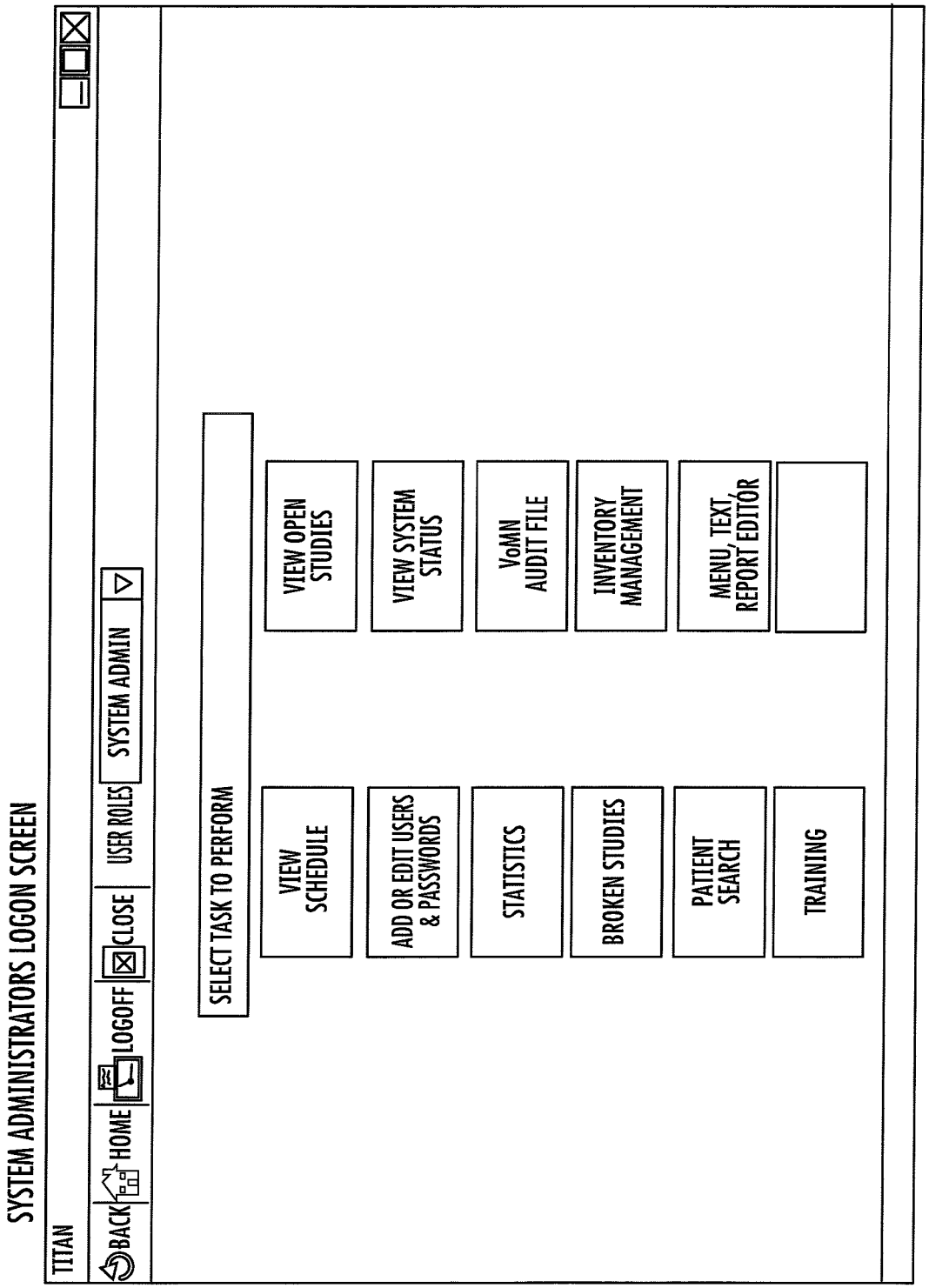
FIG. 10 shows the logon screen as displayed on a workstation of a user of a cardiovascular image and information management system, that employs the contextually sensitive, user-centric based navigation mechanism of the present invention, where the user logged into the system is a system administrator.
Figure 10A:
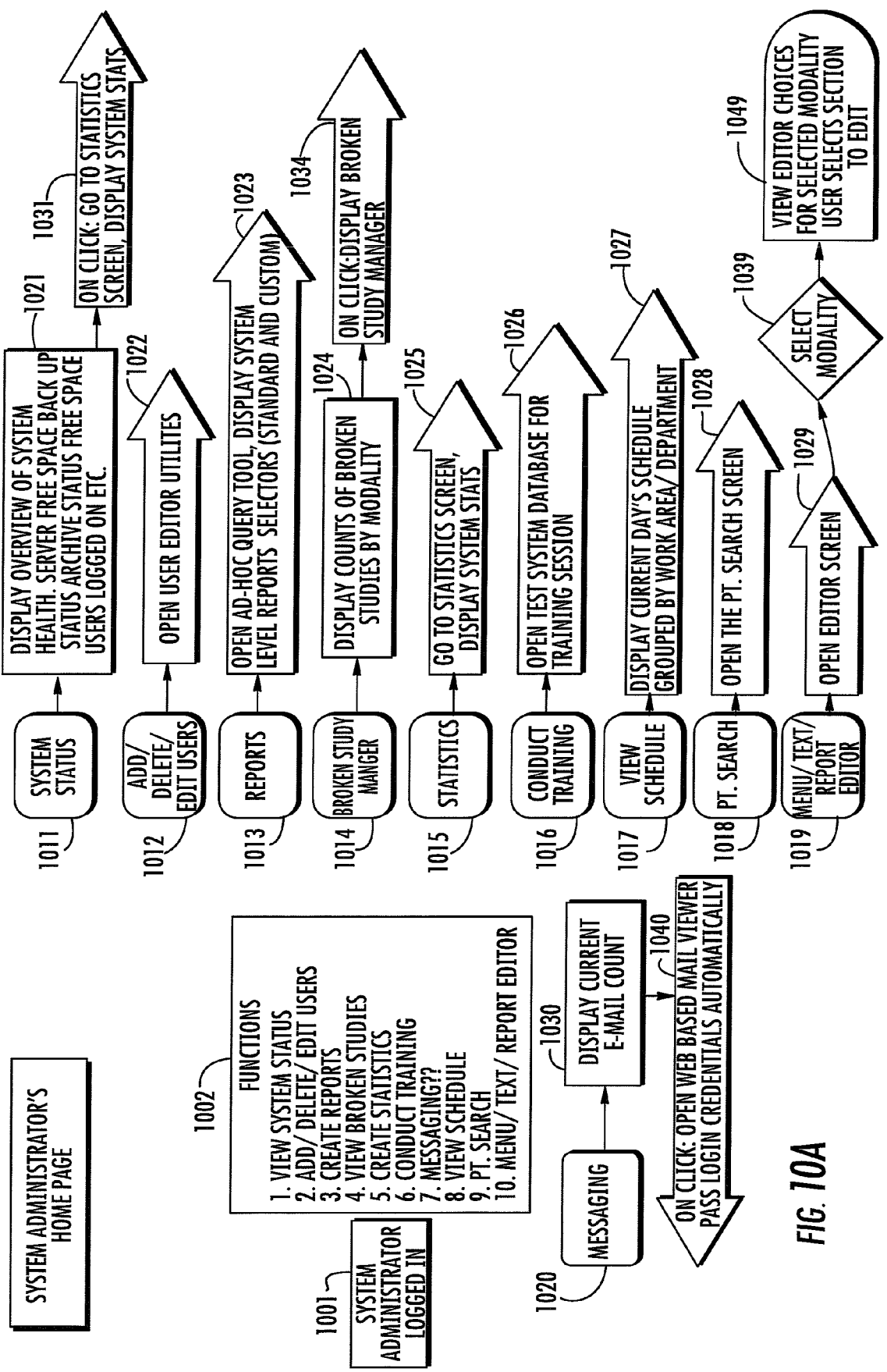
FIG. 10A shows the workflow of a system administrator associated with FIG. 10.

FIG. 10 shows the logon screen that is displayed by the workstation's display screen, while FIG. 10A shows the associated workflow, where the user logged into the system is a system administrator (shown at 1001), whose functions include those listed in block 206 in FIG. 2, described above, and repeated in the function block 1002 in FIG. 10. The system administrator controls user permissions and security, creates custom reports, resolves broken studies, and performs additional tasks, such as training the trainers. Functions that may be performed by a system administrator include a system status check 1011, adding/deleting/editing users 1012, reports 1013, a broken study manager 1014, statistics 1015, conducting training 1016, viewing schedule 1017, patient search 1018, menu/text/report editor 1019, and messaging 1020.

Invoking the system status function 1011 calls up and displays an overview of system health, including parameters that include server free space, back-up status, archive status, free space, users logged on, and the like, as shown at 1021. The user may then click on the statistics screen and display system statistics, as shown at 1031. To add, delete or edit users of the system (function 1012), the system administrator opens the user editor utilities, as shown at 1022.

The report function 1013 involves opening an ad-hoc query tool, and the display of system level reports selectors (standard and custom), as shown at 1023. When the broken study manager 1014 function is invoked, counts of broken studies are displayed according to modality, as shown at 1024. Via an on click the broken study manager may then be displayed, as shown at 1034. When the statistics function 1015 is invoked, the statistics screen is called up and displayed, as shown at 1025. To conduct training (function 1016), the system administrator opens the test system database for a training session, as shown at 1026.

When the view schedule function 1017 is invoked, the current day's schedule, grouped by work area/department, for the logged-on system administrator, is called up and displayed on the system administrator's workstation, as shown at 1027. To conduct a search for a particular patient (function 1018), the system administrator clicks on and thereby opens the patient search screen, as shown at 1028. The menu/text/report editor function 1019 is invoked by opening the screen editor at 1029; modality is selected at state 1039. At state 1049, the system administrator views editor choices for the selected modality; the system administrator then selects the section to be edited. Invoking an optional messaging function 1020, if employed, causes the current e-mail count to be displayed, as shown at 1030. The system administrator may then proceed to click on the e-mail open button, so open the web based mail viewer, which causes login credentials to be supplied automatically, as shown at 1040.

Figure 11:
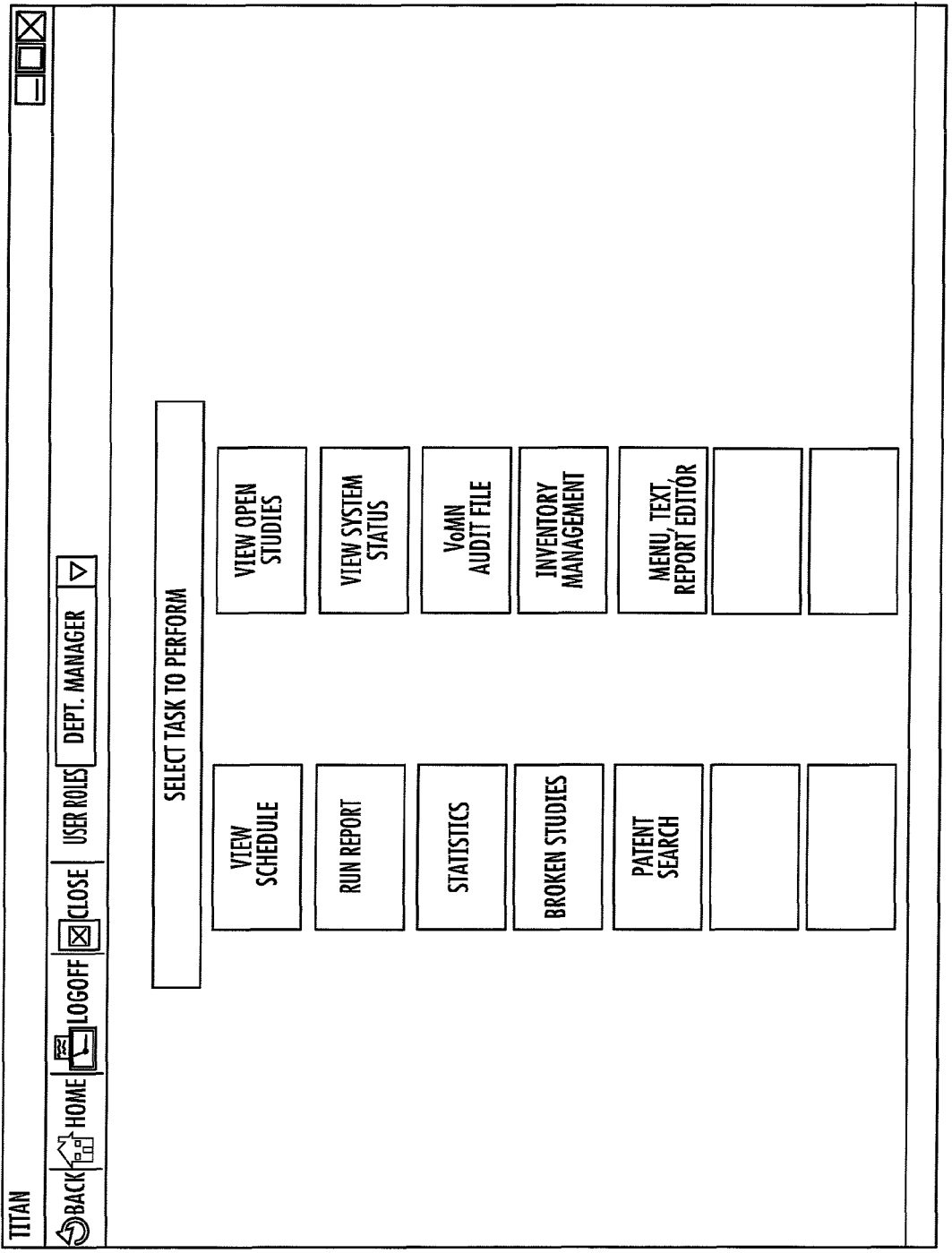
FIG. 11 shows the logon screen as displayed on a workstation of a user of a cardiovascular image and information management system, that employs the contextually sensitive, user-centric based navigation mechanism of the present invention, where the user logged into the system is a department administrator.
Figure 11A:
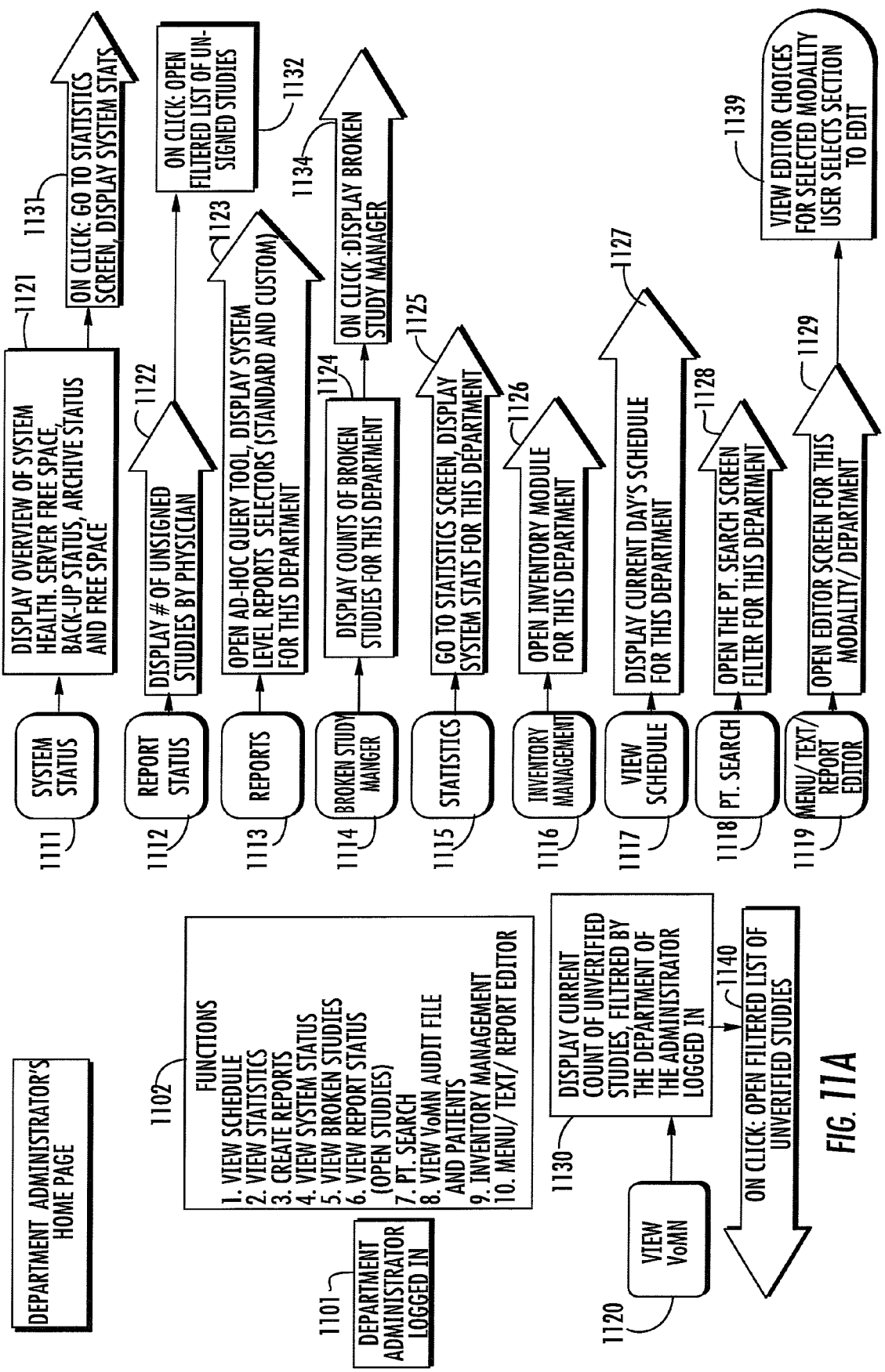
FIG. 11A shows the workflow of a department administrator associated with FIG. 11.

FIG. 11 shows the logon screen that is displayed by the workstation's display screen, where the user logged into the system is a department administrator (shown at 1101), whose functions include those listed in block 207 in FIG. 2, described above, and repeated in the function block 1102 in FIG. 11. FIG. 11A shows the associated workflow diagram. The manager or director of the cath lab, or of the cardiology department, is concerned with the efficiency and profitability of the lab or department, the reliability of all critical systems, the management of expensive inventory items, and with keeping the doctors satisfied. The functions of the department administrator include: system status 1111, report status 1112, reports 1113, broken study manager 1114, statistics 1115, inventory management 1116, view schedule 1117, patient search 1118, menu/text/report editor 1119 and view VOMN 1120.

Invoking the system status function 1111 calls up and displays an overview of system health, including parameters than include server free space, back-up status, archive status, free space, users logged on, and the like, as shown at 1121. The user may then click on the statistics screen and display system statistics, as shown at 1131. When the report status function 1112 is invoked, the number of unsigned studies is displayed by physician, at 1122. Clicking on an open button at state 1132 then opens a filtered list of unsigned studies. The report function 1113 involves opening an ad-hoc query tool, and the display of system level reports selectors (standard and custom), as shown at 1123. When the broken study manager 1114 function is invoked, counts of broken studies are displayed according to modality, as shown at 1124. Via an on click the broken study manager may then be displayed, as shown at 1134. When the statistics function 1115 is invoked, the statistics screen is called up and displayed, as shown at 1125.

Invoking the inventory management function 1116 opens an inventory module for the administrator's department, as shown at 1126. When the view schedule function 1117 is invoked, the current day's schedule, for this department, is called up and displayed on the department administrator's workstation, as shown at 1127. To conduct a search for a particular patient (function 1118), the department administrator clicks on and thereby opens the patient search screen, as shown at 1128. The menu/text/report editor function 1119 is invoked by opening the screen editor, and modality is selected at state 1129. At state 1139, the user/department administrator views editor choices for the selected modality; the department administrator then selects the section to be edited. Invoking the messaging function 1120 causes the current e-mail count to be displayed, as shown at 1130. The department administrator may then proceed to click on the e-mail open button, so open the web based mail viewer, which causes login credentials to be supplied automatically, as shown at 1140.

Figure 12B:
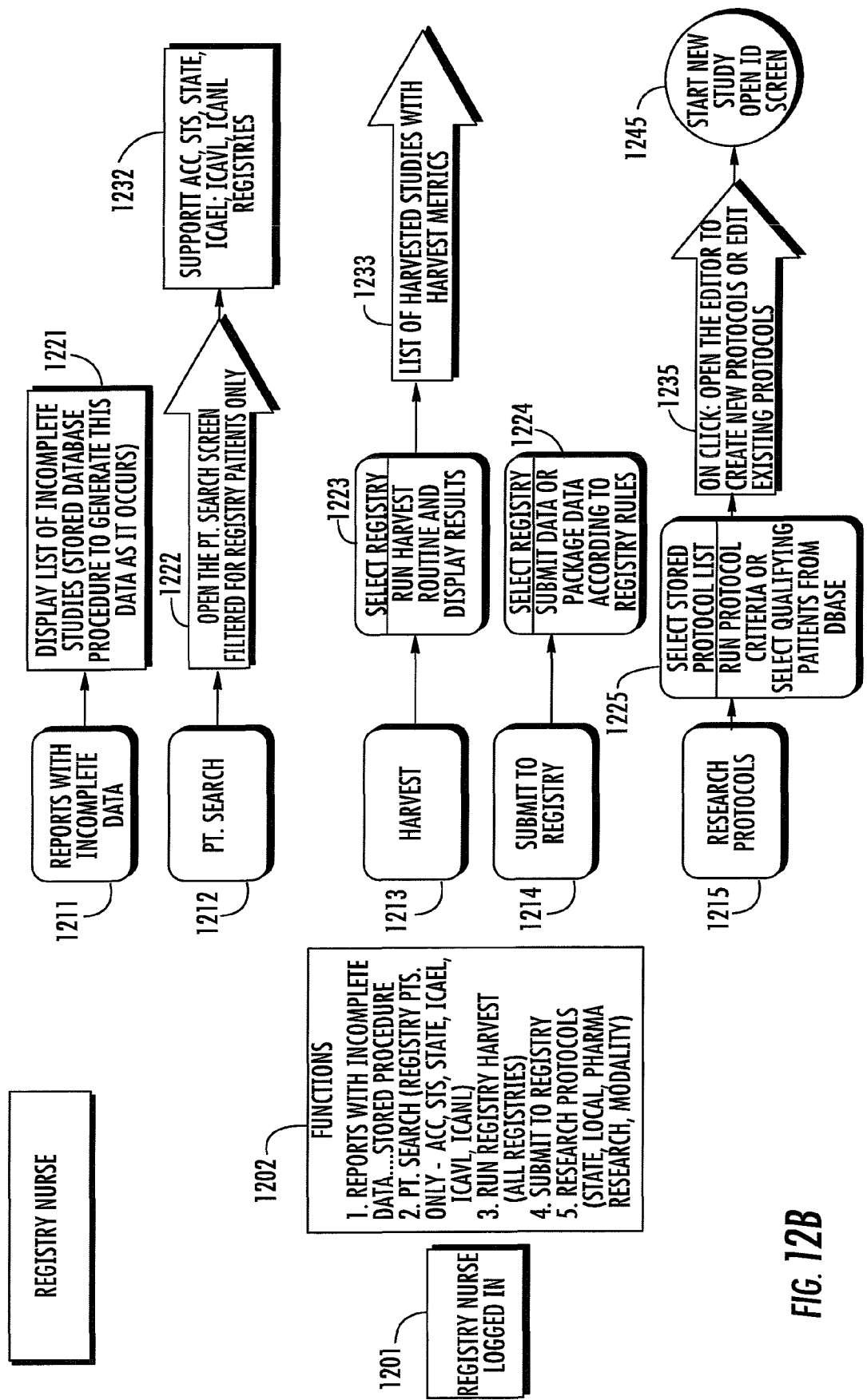
FIG. 12B shows the workflow of a registry nurse associated with the logon screen of FIG. 12.

FIG. 12 shows the logon screen that is displayed by the workstation's display screen, where the user logged into the system is a registry nurse (shown at 1201), whose functions include those listed in block 208 in FIG. 2, described above, and repeated in the function block 1202 in FIG. 12B. FIG. 12A shows an enlargement of the examples of screen fields of the logon screen of FIG. 12, while FIG. 12B shows the workflow of a registry nurse associated with the logon screen of FIG. 12. Hospitals that participate in state, regional, or national registries, employ nurses or technicians to complete the mandated registry fields in procedural reports. They then harvest the data, format it according to the unique registry instructions, and submit it on a regular basis. To this end, the functions to be performed by a registry nurse include identifying reports with incomplete data 1211, patient search 1212, harvesting 1213, submit to registry 1214, and research protocols 1215.

To identify reports with incomplete data (function 1211), a list of incomplete studies is displayed at 1221. A stored database procedure is used to generate this data as it occurs. To perform a patient search (function 1212), the patient search screen is opened and filtered for registry patients only, as shown at 1222. This serves to support ACC, STS, State, ICAEL, ICAVL, ICANL registries, as shown at 1232. To perform the harvest function 1213, the harvest routine is run on the selected registry and the results are displayed, as shown at 1223. This provides a list of harvested studies with associated harvest metrics, as shown at 1233. Invoking the submit to registry function 1214, the selected registry is supplied with data or package data according to registry rules, as shown at 1224. The research protocols function 1215 is performed by selecting the protocol from a stored protocol list, at state 1225. In addition, protocol criteria are run or qualifying patients are selected from the patient database. At 1235, the editor is opened to create new protocols or edit existing protocols. This serves to start a new study, and open an ID screen, as shown at state 1245.

Figure 13:
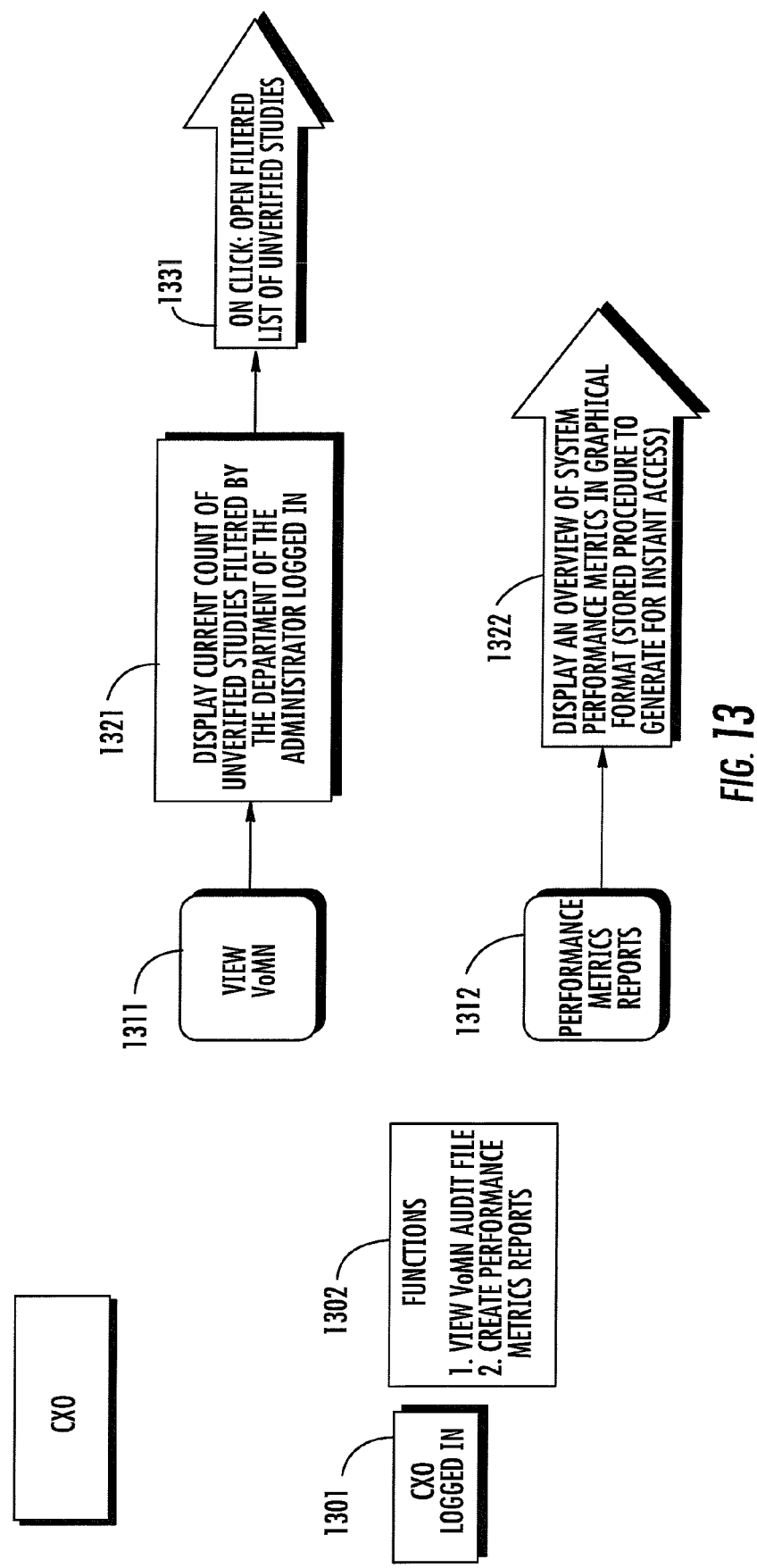
FIG. 13 shows the workflow displayed on a workstation of a user of a cardiovascular image and information management system, that employs the contextually sensitive, user-centric based navigation mechanism of the present invention, where the user logged into the system is an executive, such as the Chief Executive Officer, Chief Operating Officer, Chief Financial Officer, Chief Medical Officer, or other senior executive of the hospital.

FIG. 13 shows the workflow diagram that is displayed by the workstation's display screen, where the user logged into the system is a chief executive CXO (shown at 1301), whose functions include those listed in block 209 in FIG. 2, described above, and repeated in the function block 1302 in FIG. 13. FIG. 13A shows an example of a VOMN screen for a CXO as may be displayed by invoking function 1311 in the workflow diagram of FIG. 13. The chief executive may be the CEO, COO, CFO, VP, or risk management officer. The fiduciary nature of his/her position means that this individual is concerned with the profit/loss of his/her department, and/or the liability to which the hospital may be exposed. As a consequence, there are two principal functions listed on the homepage diagram of FIG. 13, that appeal to the CXO: 1— the performance of the cardiology department as measured by metric reports; and 2— verification of medical necessity, which will assist in reducing the hospital's vulnerability to failed Medicare audits.

These functions are identified in FIG. 13 as the view VOMN function 1311 and the performance metrics reports function 1312. When the view VOMN function 1311 is invoked, the current count of unverified studies, as filtered by the physician who performed the procedure, is displayed as shown at 1321. The CXO may then click open the filtered list of unverified studies, as shown at 1331. As described above, if the compilation of information regarding a patient and procedure reveals that the VOMN's audit file lacks one or more pieces of information to satisfy medical necessity requirements, the VOMN routine will visually alert the system user to the extent of the shortcoming and specifically tag what is lacking. This will allow the user to activate one or more objects of a user interface to initiate a search of available resources that contain the required information, so that the audit file may be completely filled in with whatever information is missing. Once the audit file complies with CMS requirements, the system will alert hospital personnel to that fact. When the CXO invokes the performance metrics reports function 1312, an overview of system performance metrics is displayed in graphical format (using a stored procedure to generate for instant access), as shown at 1322.

As will be appreciated from the foregoing description, drawbacks of conventional patient-centric data navigation and access schemes are effectively obviated by the contextually sensitive, user-centric database navigation and accessing methodology of the present invention, which facilitates navigation through and access to one or more database domains of a medical information storage and retrieval system, in particular, a cardiovascular image and information management system, based upon the specific role or function of the user. As noted above, being user-centric, rather than patient-centric, the software routine of the invention is operative to display to the user, upon logging on, a homepage that specifically pertains to the user's area of responsibility, containing a contextual list of options that are germane to the user's workflow. This facilitates the ability of the user to rapidly navigate through and access one or more data domains that are specifically relevant to the responsibilities and functions of the user, thereby improving the user's efficiency and reducing the time to complete a task, as it saves the user keystrokes and time, and effectively eliminates the frustration of trying to navigate through extraneous areas to the right place in the application.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein, but intend to cover all such changes and modifications as are obvious to one of ordinary skill in the art.

What is claimed is:

1. A computer readable medium comprising a user-centric application software routine which is executable on a system for storage and retrieval of medical information, and enables a user to navigate through and access data domains of said system, when said routine is executed on said system performs the acts of:
 (a) storing, for a first class and a second class of users of said system, plurality of user task-based database navigation subroutines which, when executed by said users, is configured to display, on a workstation of said users, one or more database information screens through which said users may navigate through and gain access to one or more selected database domains of said system; and
 (b) in response to a first user of said first class logging on to said system, displaying, on the workstation a first image-containing information elements associated with first tasks that may be carried out by the first class of the users;
 (c) in response to a second user of said second class logging on to said system, displaying, on the workstation a second image-containing information elements associated with second tasks that may be carried out by the second class of the users, the first image-containing information elements being different from the second image-containing information elements;
 wherein the first image-containing information elements have a first workflow to be followed by said first user, and wherein the second image-containing information elements have a second workflow to be followed by said second user in navigating through said one or more database domains, access to which is associated with executing a given task, the first workflow being different from the second workflow.

2. The computer readable medium of claim 1, wherein said system comprises a cardiovascular image and information management system.

3. The computer readable medium of claim 1, wherein said first class or said second class of the users include at least one of a physician, a holding area nurse, a clinician, a scheduler, an information technologist, a system administrator, a department administrator, a registry nurse, and a chief executive.

4. The computer readable medium of claim 1, wherein said first task or said second task includes at least one of scheduling, generating reports, statistics, broken study tools, patient locator/search tools, registries/research datapoints, system status monitoring, and audit logs.

5. The computer readable medium of claim 1, wherein said first and second image-containing information elements comprise a contextual list of image elements that specify said first and second tasks, respectively.

6. The computer readable medium of claim 1, wherein, in response to first image-containing information elements displayed in act (b) being selected by said first user, causing execution of a respective one of said user task-based database navigation subroutines associated with the first class of the users, so as to enable said first user to navigate through one or more database domains, access to which is associated with executing a task carried out by the first class of the users.

7. A computer readable medium comprising a user-centric application software routine which is executable on a system for storage and retrieval of medical information, for enabling a first user, who belongs to a first class of a plurality of different classes of users of said system and a second user, who belongs to a second class of the plurality of the different classes of the users of said system, to navigate through said system, and to access data domains thereof that contain information that may be required by said first and second users to complete performance of first functions and second functions, respectively, when said routine is executed on said system performs the acts of:
 (a) in response to said first user logging on to said system, displaying, on a workstation of said first user, user function-representative first information elements, associated with the first functions that may be carried out by the first class of users, the first information elements having an associated first workflow to be followed by said first user in the course of navigating through a first set of the data domains, access to which is associated with the performance of the first functions by said first user;
 (b) in response to a first information element displayed in act (a) being selected by said first user, causing the execution of a first user-centric database navigation subroutine that is operative to enable said first user to navigate through the first set of the data domains, and access therefrom information required by said first user in the course of the performance of the first functions; and
 (c) in response to a second user logging on to said system, displaying a second information element, and in response to selection by the second user of the second information element causing the execution of a second user-centric database navigation subroutine that is operative to enable said second user to navigate through a second set of the data domains, and access therefrom information required by said second user in the course of the performance of the second functions;
 wherein the first image-containing information elements have a first workflow to be followed by said first user, and wherein the second image-containing information elements have a second workflow to be followed by said second user in navigating through the second set of the data domains; and
 wherein the first image-containing information elements are different from the second image-containing information elements, and the first workflow is different from the second workflow.

8. The computer readable medium of claim 7, wherein said system comprises a cardiovascular image and information management system.

9. The computer readable medium of claim 7, wherein said first class or said second class include a physician, a holding area nurse, a clinician, a scheduler, an information technologist, a system administrator, a department administrator, a registry nurse, and a chief executive.

10. The computer readable medium of claim 7, wherein the first functions or the second function includes scheduling, generating reports, statistics, broken study tools, patient locator/search tools, registries/research datapoints, system status monitoring, and audit logs.

11. The computer readable medium of claim 7, wherein said function-representative information elements comprise a contextual list of image elements that specify said first functions and said second functions, respectively.

* * * * *